(12) United States Patent
Lok

(10) Patent No.: US 7,932,029 B1
(45) Date of Patent: Apr. 26, 2011

(54) METHODS FOR NUCLEIC ACID MAPPING AND IDENTIFICATION OF FINE-STRUCTURAL-VARIATIONS IN NUCLEIC ACIDS AND UTILITIES

(76) Inventor: Si Lok, Pokfulam (HK)

(*) Notice: Subject to any disclaimer, the term of this patent is extended or adjusted under 35 U.S.C. 154(b) by 341 days.

(21) Appl. No.: 11/649,587

(22) Filed: Jan. 3, 2007

Related U.S. Application Data

(60) Provisional application No. 60/756,417, filed on Jan. 4, 2006, provisional application No. 60/792,926, filed on Apr. 17, 2006, provisional application No. 60/814,378, filed on Jun. 15, 2006.

(51) Int. Cl.
C12Q 1/68 (2006.01)
C07H 21/02 (2006.01)
C07H 21/04 (2006.01)

(52) U.S. Cl. .......................... 435/6; 536/23.1; 536/24.3

(58) Field of Classification Search ..... 435/6; 536/23.1, 536/24.3
See application file for complete search history.

(56) References Cited

U.S. PATENT DOCUMENTS

| | | | | |
|---|---|---|---|---|
| 4,634,678 A | * | 1/1987 | Salstrom et al. | 435/320.1 |
| 5,376,549 A | * | 12/1994 | Guilfoyle et al. | 435/320.1 |
| 5,508,169 A | * | 4/1996 | Deugau et al. | 435/6 |
| 5,512,463 A | * | 4/1996 | Stemmer | 435/91.2 |
| 5,624,826 A | * | 4/1997 | Kato et al. | 435/91.4 |
| 5,695,937 A | * | 12/1997 | Kinzler et al. | 435/6 |
| 5,707,807 A | * | 1/1998 | Kato | 435/6 |
| 5,763,175 A | * | 6/1998 | Brenner | 435/6 |
| 5,821,118 A | * | 10/1998 | Omer et al. | 435/320.1 |
| 5,830,645 A | | 11/1998 | Pinkel et al. | |
| 5,888,737 A | * | 3/1999 | DuBridge et al. | 435/6 |
| 6,136,537 A | * | 10/2000 | Macevicz | 435/6 |
| 6,383,754 B1 | * | 5/2002 | Kaufman et al. | 435/6 |
| 6,709,861 B2 | | 3/2004 | Mead et al. | |
| 6,730,500 B1 | | 5/2004 | Lok | |
| 7,115,407 B2 | * | 10/2006 | Morgan et al. | 435/199 |
| 7,186,538 B2 | * | 3/2007 | Morgan et al. | 435/199 |
| 2002/0028458 A1 | * | 3/2002 | Lexow | 435/6 |
| 2002/0102670 A1 | * | 8/2002 | Livshits et al. | 435/116 |
| 2003/0119053 A1 | * | 6/2003 | Maine et al. | 435/7.1 |
| 2003/0144490 A1 | * | 7/2003 | Edwards et al. | 536/23.1 |
| 2003/0186239 A1 | * | 10/2003 | Dhallan | 435/6 |
| 2005/0100900 A1 | * | 5/2005 | Kawashima et al. | 435/6 |
| 2006/0140911 A1 | * | 6/2006 | Sharp et al. | 424/93.6 |
| 2009/0005266 A1 | * | 1/2009 | Ostermeier et al. | 506/17 |
| 2009/0325239 A1 | * | 12/2009 | Lok | 435/91.2 |
| 2010/0159534 A1 | * | 6/2010 | Morgan | 435/91.53 |

OTHER PUBLICATIONS

Tuzun et al., Fine-scale structural variation of the human genome. Nature Genetics 37 (7) : 727-732 (Jul. 2005).*
Velculescu et al, Serial Analysis of Gene Expression. Science 270 : 484-487 (1995).*
Pingoud et al., Structure and function of type II restriction endonucleases. Nucleic Acids Research 29(18) : 3705-3727 (2001).*
Sears et al., Characterization of the type III restriction endonuclease PstIII from *Providencia stuartii*. Nucleic Acids Research 33(15) : 4775-4787 (2005).*
Rouillard et al., Virtual Genome Scan : A tool for restriction Landmark- based scanning of the human genome. Genome Research 11 : 1453-1459 (2001).*
Kent et al. Assembly of the working draft of the human genome with GigAssembler. Genome Research 11: 1541-1548 (2001).*
Mullikin et al., The phusion assembler.Genome Research 13: 81-90 (2003).*
Roach et al. Pairwise end sequencing : A unified approach to genoimic mapping and sequencing. Genomics 26 : 345-353 (1995).*
Dryden et al., Nucleoside triphosphate-dependent restriction enzymes Nucleic Acids Research 29 (18) : 3728-3741 (2001).*
Jobling et al., Construction of vectors with the p15a replicon, kanamycin resistance, inducible lacZ alpha and pUC18 or pUC19 multiple cloning sites. Nucleic Acids Research 18 (17) : 5315-5316 (1990).*
Meisel et al., Type III restriction enzymes need two inversely oriented recognition sites for DNA cleavage. Nature 355 :467-469 (1992).*
pUC18, pUC19 (2000).*
Szybalski et al., Class-IIS restriction Enzymes—a review. Gene 100: 13-26 (1991).*
Buryanov, Y.I. et al.; *Site Specificity and Chromatographic Properties of E. coli K12 ans EcoRII DNA-Cytosine Methylases*; FEBS Letters 88:251, (1978).
Albertson, D.G. et al.; *Quantitative Mapping of Amplicon Structure by Array CHJ Identifies CYP24 as a Candidate Oncogene*; Nature America Inc. 25:144, (2000).
Albertson, D.C. and Pinkel, D.; *Genomic Microarrays in Human Genetic Disease and Cancer*; Human Molecular Genetics, Review Issue 12:145, (2003).
Andersson, L.; *Genetic Dissection of Phenotypic Diversity in Farm Animals*; Nature Genetics 2:130, (2001).
Bailey, J.A. et al.; *Recent Segmental Duplications in the Human Genome*; Science 297:1003, (2002).
Bignell, G.R. et al.; *High-Resolution Analysis of DNA Copy Number Using Oligonucleotide Microarrays*; Genome Research 14:287, (2004).
Bolivar, F. et al.; *Construction and Characterization of New Cloning Vehicles .II. A Multipurpose System*; Gene 2:95, (1977) (Abstract Only).
Boyd, A.C. et al.; *Isolation and Computer-Aided Characterization of MmeI, a Type II Restriction Endonuclease from Methylophilus Methylotrophus*; Nucleic Acids Research 14:5255, (1986).
Brennan, C. et al.; *High-Resolution Global Profiling of Genomic Alterations with Long Oligonucletide Microarray*; Cancer Research 64:4744, (2004).
Bujnicki, J.M.; *Understanding the Evolution of Restriction-Modification Systems: Clues from Sequence and Structure Comparisons*; Acta Biochimica Polonica 48:935, (2001). Chang, A.C.; *Construction and Characterization of Amplifiable Multicopy DNA Cloning Vehicles Derived from the P15A Cryptic Miniplasmid*; Journal of Bacteriology 134:1141, (1978).
Check, E.; *Patchwork People*; Nature 437:1084, (2005).
Cheng, Z. et al.; *A Genome-Wide Comparison of Recent Chimpanzee and Human Segmental Duplications*; Nature 437:88, (2005).
Collins, F.S. and Weissman, S.M.; *Directional Cloning of DNA Fragments at a Large Distance from an Initial Probe: A Circularization Method*; Proc.Natl.Acad.Sci USA 81:6812, (1984).

(Continued)

*Primary Examiner* — Ethan Whisenant
(74) *Attorney, Agent, or Firm* — Saliwanchik, Lloyd & Eisenschenk

(57) ABSTRACT

The invention disclosed herein describes methods for the mapping and identification of fine-structural variations in nucleic acids.

41 Claims, No Drawings

OTHER PUBLICATIONS

Collins, F.S. et al.; *Construction of a General Human Chromosome Jumping Library, with Applications to Cystic Fibrosis*; Science 235:1046, (1987) (Abstract Only).

Craddock, N. and Jones, I.; *Molecular Genetics of Bipolar Disorder*; Br. J Psychiatry Suppl. 41:128, (2001) (Abstract Only).

Deininger, P.L.; *Random Subcloning of Sonicated DNA: Application to Shotgun DNA Sequence Analysis*; Analytical Biochemistry 129:216, (1983).

Dugaiczyk, A. et al.; *Ligation of EcoRI Endonuclease-Generated DNA Fragments Into Linear and Circular Structures*; Journal of Molecular Biology 96:171, (1975).

Dunn, J.J. et al.; *Genomic Signature Tags (GSTs): A System for Profiling Genomic DNA*; Genome Research 12:1756, (2002).

Feng, T. et al.; *Increased Efficiency of Cloning Large DNA Fragments Using a Lower Copy Number Plasmid*; Bio Techniques 32:992, (2002).

Feuk, L. et al.; *Structural Variation in the Human Genome*; Nature Review Genetics 7:85, (2006).

Fitzgerald, M.C. et al.; *Rapid Shotgun Cloning Utilizing the Two Base Recognition Endonuclease CviJI*; Nucleic Acids Research 20:3753, (1992).

Geier, G.E. and Modrich, P.; *Recognition Sequence of the dam Methylase of Escherichia coli K12 and Mode of Cleavage of Dpn I Endonuclease*; The Journal of Biological Chemistry 254:1408, (1979).

Gonzalez, E. et al.; *The Influence of CCL3L1 Gene-Containing Segmental Duplications on HIV1/AIDS Susceptibility*; Science 307:1434, (2005).

Gray, J.W. and Collins, C.; *Genome Changes and Gene Expression in Human Solid Tumors*; Carcinogenesis 21:443, (2000).

Grindley, N. D.F. and Joyce C.M.; *Genetic and DNA Sequence Analysis of the Kanamycin Resistance Transposon Tn903*; Proc. Natl. Acad. Sci. USA 77:7176, (1980).

Hamlin, C. and Yelle, J.; *Gel and Buffer Effects on the Migration of DNA Molecules in Agarose*; Appl. Theor. Electrophor. 5:225, (1990) (Abstract Only).

Harrison B. and Zimmerman S.B.; *Polymer-Stimulated Ligation: Enhanced Ligation of Oligo- and Polynucleotides by T4 RNA Ligase in Polymer Solutions*; Nucleic Acids Research 12:21, (1984).

Hattman S. et al.; *Sequence Specificity of the P1 Modification Methylase (M.Eco P1) and the DNA Methylase (M.Eco dam) Controlled by the Escherichia coli Dam Gene*; Journal of Molecular Biology 126:367, (1978).

Heffron F. et al.; *In Vitro Mutagenesis of a Circular DNA Molecule by Using Synthetic Restriction Sites*; Proc.Natl.Acad.Sci. USA 75:6012, (1978).

Heiskanen M.A. et al.; *Detection of Gene Amplification by Genomic Hybridization to cDNA Microarrays*; Cancer Research 60:799, (2000).

Holzman P.S. et al.; *The Genetics of Schizophrenia: A Review*; Psychological Science 1:279, (1990) (Abstract Only).

Honeybee Genome Sequencing Consortium; *Insights Into Social Insects from the Genome of the Honeybee Apis Mellifera*; Nature 443:931, (2006).

Huang J. et al.; *Whole Genome DNA Copy Number Changes Idetifies by High Density Oligonucleotide Arrays*; Hum Genomics 4:287, (2004) (Abstract Only).

Inazawa J. et al.; *Comparative Genomic Hybridization (CGH)-Arrays Pave the Way for Identification of Novel Cancer-Related Genes*; Cancer Sci 95:559, (2004).

Kan N. C. et al.; *The Nucleotide Sequence Recognized by the Escherichia coli K12 Restriction and Modification Enzymes*, Journal of Molecular Biology 130:191, (1979).

Kozdroj J. et al.; *Structural Diversity of Microorganism in Chemically Perturbed Soil Assessed by Molecular and Cytochemical Approaches*; Journal of Microbiological Methods 43:197, (2001).

Lucito R. et al.; *Representational Oligonucleotide Microarray Analysis: A High-Resolution Method to Detect Genome Copy Number Variation*; Genome Research 13:2291, (2003).

Mackay T.F.C.; *Quantitative Trait Loci in Drosophila*; Nature Review Genetics 2:11, (2001) (Abstract Only).

Matsumura H. et al.; *Gene Expression Analysis of Plant Host-Pathogen Interactions by SuperSAGE*; PNAS 100:15718, (2003).

May M.S. et al.; *Analysis of Bacteriophage Deozyribonucleic Acid Sequences Methylated by Host-and R-Factor-Controlled Enzymes*; Journal of Bacteriology 123:768, (1975).

McClelland M. et al.; *Effect of Site-Specific Modification on Restriction Endonucleases and DNA Modification Methyltransferases*; Nucleic Acids Research 22:3640, (1994).

Melgar E. et al.; *Deoxyribonucleic Acid Nucleases*; The Journal of Biological Chemistry 243:4409, (1968).

Mucke M. et al.; *DNA Cleavage by Type III Restriction-Modification Enzyme EcoP15I is Independent of Spacer Distance Between Two Head Oriented Recognition Sites*; J.Mol.Biol. 312:687, (2001).

Ng P. et al.; *Gene Identification Signature (GIS) Analysis for Transcriptome Characterization and Genome Annotation*; Nature Methods 2:105, (2005).

Owen M.J. et al.; *Modern Molecular Genetic Approaches to Complex Traits*; Mol. Psychiatry 1:21, (1996) (Abstract Only).

Peakman L.J. et al.; *S-Adenosyl Methionine Prevents Promiscuous DNA Cleavage by the EcoPII Type III Restriction Enzyme*; J.Mol. Biol. 333:321, (2003).

Pheiffer B.H. et al.; *Polymer-Stimulated Ligation: Enhanced Blunt- or Cohesive-end Ligation of DNA or Deoxyribooligonucleotides by T4 DNA Ligase in Polymer Solutions*; Nucleic Acids Research 11:7853, (1983).

Pinkel D. et al.; *High Resolution Analysis of DNA Copy Number Variation Using Comparative Genomic Hibridization to Microarrays*; Nature Genetics 20:207, (1998).

Pinkel D. and Albertson D.G.; *Array Comparative Genomic Hybridization and its Applications in Cancer*; Nature Genetics Supp. 37:S11, (2005).

Pollack J.R. et al.; *Genome-Wide Analysis of DNA Copy-Number Chnages Using cDNA Microarrays*; Nature Genetics 23:41, (1999).

Pollack J.R. et al.; *Microarrays Analysis Reveals a Major Direct Role of DNA Copy Number*; PNAS USA 99:12963, (2002).

Redon R. et al.; *Global Variation in Copy Number In the Human Genome*; Nature 444:444, (2006).

\* cited by examiner

```
                        SEQUENCE LISTING

<160> NUMBER OF SEQ ID NOS: 28

<210> SEQ ID NO 1
<211> LENGTH: 17
<212> TYPE: DNA
<213> ORGANISM: Artificial sequence
<220> FEATURE:
<223> OTHER INFORMATION: Chemically synthesized oligonucleotide

<400> SEQUENCE: 1
gacacagagg atccaac                                                17

<210> SEQ ID NO 2
<211> LENGTH: 13
<212> TYPE: DNA
<213> ORGANISM: Artificial sequence
<220> FEATURE:
<223> OTHER INFORMATION: Chemically synthesized oligonucleotide

<400> SEQUENCE: 2
gttggatcct ctg                                                    13

<210> SEQ ID NO 3
<211> LENGTH: 17
<212> TYPE: DNA
<213> ORGANISM: Artificial sequence
<220> FEATURE:
<223> OTHER INFORMATION: Chemically synthesized oligonucleotide

<400> SEQUENCE: 3
ctaggttgga tcctctg                                                17

<210> SEQ ID NO 4
<211> LENGTH: 17
<212> TYPE: DNA
<213> ORGANISM: Artificial sequence
<220> FEATURE:
<223> OTHER INFORMATION: Chemically synthesized oligonucleotide

<400> SEQUENCE: 4
gacacagact gcagcag                                                17

<210> SEQ ID NO 5
<211> LENGTH: 13
<212> TYPE: DNA
<213> ORGANISM: Artificial sequence
<220> FEATURE:
<223> OTHER INFORMATION: Chemically synthesized oligonucleotide

<400> SEQUENCE: 5
ctgctgcagt ctg                                                    13

<210> SEQ ID NO 6
<211> LENGTH: 17
<212> TYPE: DNA
<213> ORGANISM: Artificial sequence
<220> FEATURE:
<223> OTHER INFORMATION: Chemically synthesized oligonucleotide

<400> SEQUENCE: 6
```

```
ctagctgctg cagtctg                                              17
```

<210> SEQ ID NO 7
<211> LENGTH: 46
<212> TYPE: DNA
<213> ORGANISM: Artificial sequence
<220> FEATURE:
<223> OTHER INFORMATION: Chemically synthesized oligonucleotide

<400> SEQUENCE: 7

```
aattggacaa gagacggaat attctagaac gatacgtctc ctgtcc              46
```

<210> SEQ ID NO 8
<211> LENGTH: 46
<212> TYPE: DNA
<213> ORGANISM: Artificial sequence
<220> FEATURE:
<223> OTHER INFORMATION: Chemically synthesized oligonucleotide

<400> SEQUENCE: 8

```
aattggacag gagacgtatc gttctagaat atgccgtctc ttgtcc              46
```

<210> SEQ ID NO 9
<211> LENGTH: 56
<212> TYPE: DNA
<213> ORGANISM: Artificial sequence
<220> FEATURE:
<223> OTHER INFORMATION: Chemically synthesized oligonucleotide

<400> SEQUENCE: 9

```
gagagacaag agacggcatc tcagtagtct agaagtgcac gatagcgtct cctgtc    56
```

<210> SEQ ID NO 10
<211> LENGTH: 55
<212> TYPE: DNA
<213> ORGANISM: Artificial sequence
<220> FEATURE:
<223> OTHER INFORMATION: Chemically synthesized oligonucleotide

<400> SEQUENCE: 10

```
aacgacagga gacgctatcg tgcacttcta gactactgag atgccgtctc ttgtc     55
```

<210> SEQ ID NO 11
<211> LENGTH: 56
<212> TYPE: DNA
<213> ORGANISM: Artificial sequence
<220> FEATURE:
<223> OTHER INFORMATION: Chemically synthesized oligonucleotide

<400> SEQUENCE: 11

```
gagtctgatg agaccctagc ctcttgagtc gaccactata catcaggtct cctcag    56
```

<210> SEQ ID NO 12
<211> LENGTH: 56
<212> TYPE: DNA
<213> ORGANISM: Artificial sequence
<220> FEATURE:
<223> OTHER INFORMATION: Chemically synthesized oligonucleotide

<400> SEQUENCE: 12

```
tcacctgagg agacctgatg tatagtggtc gactcaagag gctagggtct catcag    56
```

<210> SEQ ID NO 13
<211> LENGTH: 20
<212> TYPE: DNA
<213> ORGANISM: Artificial sequence
<220> FEATURE:

-continued

<223> OTHER INFORMATION: Chemically synthesized sequencing primer

<400> SEQUENCE: 13
taatacgact cactataggg                                                20

<210> SEQ ID NO 14
<211> LENGTH: 20
<212> TYPE: DNA
<213> ORGANISM: Artificial sequence
<220> FEATURE:
<223> OTHER INFORMATION: Chemically synthesized sequencing primer

<400> SEQUENCE: 14
attaaccctc actaaaggga                                                20

<210> SEQ ID NO 15
<211> LENGTH: 19
<212> TYPE: DNA
<213> ORGANISM: Artificial sequence
<220> FEATURE:
<223> OTHER INFORMATION: Chemically synthesized sequencing primer

<400> SEQUENCE: 15
cacgacgttg taaaacgac                                                 19

<210> SEQ ID NO 16
<211> LENGTH: 20
<212> TYPE: DNA
<213> ORGANISM: Artificial sequence
<220> FEATURE:
<223> OTHER INFORMATION: Chemically synthesized sequencing primer

<400> SEQUENCE: 16
ggataacaat ttcacacagg                                                20

<210> SEQ ID NO 17
<211> LENGTH: 48
<212> TYPE: DNA
<213> ORGANISM: Artificial sequence
<220> FEATURE:
<223> OTHER INFORMATION: Chemically synthesized oligonucleotide
<220> FEATURE:
<221> NAME/KEY: misc_feature
<222> LOCATION: (9)..(44)
<223> OTHER INFORMATION: n is a, c, g, or t

<400> SEQUENCE: 17
gatccaacnn nnnnnnnnn nnnnnnnnnn nnnnnnnnnn nnnngttg                  48

<210> SEQ ID NO 18
<211> LENGTH: 48
<212> TYPE: DNA
<213> ORGANISM: Artificial sequence
<220> FEATURE:
<223> OTHER INFORMATION: Chemically synthesized oligonucleotide
<220> FEATURE:
<221> NAME/KEY: misc_feature
<222> LOCATION: (9)..(44)
<223> OTHER INFORMATION: n is a, c, g, or t

<400> SEQUENCE: 18
gatccaacnn nnnnnnnnn nnnnnnnnnn nnnnnnnnnn nnnngttg                  48

<210> SEQ ID NO 19
<211> LENGTH: 66
<212> TYPE: DNA
<213> ORGANISM: Artificial sequence
<220> FEATURE:

<223> OTHER INFORMATION: Chemically synthesized oligonucleotide
<220> FEATURE:
<221> NAME/KEY: misc_feature
<222> LOCATION: (5)..(58)
<223> OTHER INFORMATION: n is a, c, g, or t

<400> SEQUENCE: 19
gcagnnnnnn nnnnnnnnnn nnnnnnnnnn nnnnnnnnnn nnnnnnnnnn nnnnnnnnct    60
gctgca                                                               66

<210> SEQ ID NO 20
<211> LENGTH: 66
<212> TYPE: DNA
<213> ORGANISM: Artificial sequence
<220> FEATURE:
<223> OTHER INFORMATION: Chemically synthesized oligonucleotide
<220> FEATURE:
<221> NAME/KEY: misc_feature
<222> LOCATION: (5)..(58)
<223> OTHER INFORMATION: n is a, c, g, or t

<400> SEQUENCE: 20
gcagnnnnnn nnnnnnnnnn nnnnnnnnnn nnnnnnnnnn nnnnnnnnnn nnnnnnnnct    60
gctgca                                                               66

<210> SEQ ID NO 21
<211> LENGTH: 18
<212> TYPE: DNA
<213> ORGANISM: Artificial sequence
<220> FEATURE:
<223> OTHER INFORMATION: Chemically synthesized oligonucleotide

<400> SEQUENCE: 21
gacacacgtg ctagtccg                                                  18

<210> SEQ ID NO 22
<211> LENGTH: 18
<212> TYPE: DNA
<213> ORGANISM: Artificial sequence
<220> FEATURE:
<223> OTHER INFORMATION: Chemically synthesized oligonucleotide

<400> SEQUENCE: 22
gatccggact agcacgtg                                                  18

<210> SEQ ID NO 23
<211> LENGTH: 22
<212> TYPE: DNA
<213> ORGANISM: Artificial sequence
<220> FEATURE:
<223> OTHER INFORMATION: Chemically synthesized oligonucleotide

<400> SEQUENCE: 23
gacacacgtg ctagtccctg ca                                             22

<210> SEQ ID NO 24
<211> LENGTH: 14
<212> TYPE: DNA
<213> ORGANISM: Artificial sequence
<220> FEATURE:
<223> OTHER INFORMATION: Chemically synthesized oligonucleotide

<400> SEQUENCE: 24
gggactagca cgtg                                                      14

<210> SEQ ID NO 25

```
<211> LENGTH: 18
<212> TYPE: DNA
<213> ORGANISM: Artificial sequence
<220> FEATURE:
<223> OTHER INFORMATION: Chemically synthesized oligonucleotide

<400> SEQUENCE: 25
ctgacacgtg ctagtccg                                                  18

<210> SEQ ID NO 26
<211> LENGTH: 18
<212> TYPE: DNA
<213> ORGANISM: Artificial sequence
<220> FEATURE:
<223> OTHER INFORMATION: Chemically synthesized oligonucleotide

<400> SEQUENCE: 26
gatccggact agcacgtg                                                  18

<210> SEQ ID NO 27
<211> LENGTH: 22
<212> TYPE: DNA
<213> ORGANISM: Artificial sequence
<220> FEATURE:
<223> OTHER INFORMATION: Chemically synthesized oligonucleotide

<400> SEQUENCE: 27
ctgacacgtg ctagtccctg ca                                             22

<210> SEQ ID NO 28
<211> LENGTH: 14
<212> TYPE: DNA
<213> ORGANISM: Artificial sequence
<220> FEATURE:
<223> OTHER INFORMATION: Chemically synthesized oligonucleotide

<400> SEQUENCE: 28
gggactagca cgtg                                                      14
```

METHODS FOR NUCLEIC ACID MAPPING AND IDENTIFICATION OF FINE-STRUCTURAL-VARIATIONS IN NUCLEIC ACIDS AND UTILITIES

CROSS REFERENCE TO RELATED APPLICATIONS

This application claims priority based upon U.S. Provisional Patent Applications U.S. Ser. Nos. 60/756,417 filed 4 Jan. 2006; 60/792,926 filed 17 Apr. 2006; and 60/814,378 filed 15 Jun. 2006. The entire contents of the foregoing provisional applications are incorporated herein by reference.

FIELD OF THE INVENTION

The present invention relates generally to methods for high-throughput analysis of fine structural variations in nucleic acids. In particular, the present invention relates to novel strategies, vector and vector components to produce pairs of linked-nucleic acid tags, wherein constituent members of a linked nucleic acid tag-pair are of a user defined separation distance, and/or are markers of nucleic acid positions that demarcate adjacent cleavage sites for one or more different restriction endonucleases along the length of a target nucleic acid molecule.

BACKGROUND OF THE INVENTION

While the most abundant type of variant in the Human genome and the best-studied is the single-nucleotide polymorphism (SNP), it is increasingly clear that the so termed "fine-structural-variations" comprising alterations of copy number (insertions, deletions and duplications), inversions, translocations and other sequence rearrangements are integral features of the Human and other genomes. These types of variations appear present in much greater frequency in the general population than originally thought. Evidence is mounting to indicate that structural variants can comprise millions of nucleotides of heterogeneity within every genome. Understanding the role of fine-structural-variations in genome evolution, interaction with the environment, phenotypic diversity and in disease or disease susceptibility are among the most actively investigated areas of current genomic research. For review, refer to Bailey et al. (*Science* 297:1001 (2002)), Check (*Nature* 437:1094 (2005)), Cheng et al. (*Nature* 437:88 (2005)), and Feuk et al. (*Nat Reviews* 7:85 (2006), Redon et al. (*Nature* 444: 444 (2006)).

In comparison to analysis of SNPs, efficient high throughput methods for analysis of fine-structural-variations are not well developed. An important first step is the technique of array comparative genomic hybridization (array CGH) (Pinkel et al. *Nat Genet* 20:207 (1998); Pinkel et al. U.S. Pat. Nos. 5,830,645 and 6,159,685), which enables the qualification of relative copy numbers between target DNA and reference DNA. Array CGH allows reliable detection of deoxyribonucleic acid (DNA) copy-number differences between DNA or genomic samples with the resolution at the level of a single arrayed bacterial artificial chromosome (BAC) clone (Pinkel et al. *Nat Genet* 20: 207 (1998); Albertson et al. *Nat Genet* 25:144 (2000); Snijders et al. *Nat Genet* 29:263 (2001)). The adaptation of array CGH to cDNA (Heiskanen et al. *Cancer Res* 60:799 (2000); Pollack et al. *Nat Genet* 23:41 (1999)) and to high-density oligo-nucleotide array platforms (Brennan et al. *Cancer Res* 64:4744 (2004); Lucito et al. *Genome Res* 13:2291 (2003); Bignell et al. *Genome Res* 14:287 (2004); Hung et al. *Hum Genomics* 1:287 (2004)) further extends the resolution and utility for this approach. Through its use, array CGH has led to the identification of gene copy number alterations that are associated with tumor (Inazawa et al. *Cancer Sci* 7:559 (2004); Pinkel and Albertson *Nat Genet* 37 suppl:S11 (2005); Pollack et al. *Proc Natl Acad Sci USA* 99:12963 (2002); Albertson and Pinkel *Hum Mol Genet* 12 Spec No 2: R145 (2003)) and disease progression (Gonzalez et al. *Science* 307:5714 (2005)).

Despite the usefulness for copy number determination, array CGH is not suited to address the other types of genomic structural variations, most notably, inversions, translocations and other types of nucleic acid rearrangements. Tuzun et al. (*Nat Genet* 37:727 (2005)) attempt to address these limitations with an approach termed "fosmid paired-end mapping." This approach relies on the head-full mechanism of fosmid packaging to produce genomic DNA libraries with reasonably uniform ~40 kb size genomic inserts from test subjects. End-terminal sequencing of the randomly selected ~40 kb library inserts produces pairs of short sequence tags in which each tag-pair marks two genomic positions with separation of approximately 40 kb along the lengths of the target DNA. The tag-pairs are then computationally aligned to a reference genomic assembly and any discordance with either their expected orientation or with their ~40 kb separation distance, would denote the presence of at least one structural difference between target and reference nucleic acid spanning that region. Tag-pairs having map positions that are separated by more than 40 kb signify the presence of a deletion on the target DNA in respect to the reference; map positions with separation of less than 40 kb signify an insertion of DNA in the target. Inconsistencies in the orientation of the pair of mapped tags denote potential DNA inversions or other complex chromosomal rearrangements. Chromosomal translocations are signified by assignment of the tag-pair to two different chromosomes on the reference sequence. Analysis of over 1.1 million fosmid clone inserts enabled Tuzun et al. (*Nat Genet* 37:727 (2005)) to identify nearly 300 sites of structural variations between test subject and the reference genomic assembly.

While fosmid paired-end mapping is a useful start to identify fine-structural-variations in the Human Genome, the immense cost and logistical efforts required to purify and sequence more than a million fosmid insert ends for each test subject preclude its use in broad population and cohort surveys to identify genomic variations that could be associated with complex disease or in response to environmental factors and the like. Furthermore, fosmid vectors and their variants generally propagate in very low copy-numbers in host cells making reliable automated DNA production and sequencing difficult to maintain. Hence, there is a need for an efficient, robust high throughput and low cost method for the identification of fine-structural-variations for use in genomic and association studies to link these genetic elements to disease, disease progression and disease susceptibility. The present invention provides these and other substantial benefits.

SUMMARY OF THE INVENTION

The present invention provides novel improved high throughput methods, vectors, and vector components to screen and to identify fine-structural-variations in nucleic acid populations. The invention creates pairs of short juxtaposing sequence tags termed Genomic Variation Tags (GVTs), where constituent members of a GVT-pair are of a user defined separation distance, and/or are markers to positions that demarcate adjacent sites for one or more different restriction endonucleases along the length of a nucleic acid molecule under investigation.

When individual GVTs of a GVT-pair are aligned computationally onto a reference sequence, any discordance with their expected identity, separation distance and/or orientation from the reference sequence denotes the presence of one or more fine-structural-differences between target and reference nucleic acids in the region spanned by the GVT-pair. In this way a comprehensive library of GVT-pairs represents a genomic profile that can be used to generate high-resolution structural maps to identify fine-structural-variations between nucleic acid populations. Another aspect of the invention enables the user to define and to alter the separation distance on a nucleic acid population tagged by the GVT-pairs allowing the creation of GVT-pair libraries that are tailored to detect fine-structural-variations at different spatial resolutions and coverage. Another aspect of the invention produces GVT-pairs that are markers to positions immediately proximal to pairs of adjacent recognition sites for one or more different restriction endonucleases along the length of the nucleic acid under investigation. Another aspect of the invention produces GVT-pairs that are markers to positions immediately proximal to pairs of adjacent recognition sites for one or more different restriction endonucleases along the length of the nucleic acid that are separated by a user defined distant along the length of the nucleic acid under investigation. Yet another aspect of the invention provides methods to oligomerize created GVT-pairs efficiently and to propagate the resulting oligomer stably in an optimized vector and host systems to facilitate efficient high-throughput sequence determination of GVT-pairs.

According to the present invention, DNA of a target population for analysis is fragmented either randomly or at defined sites. In certain embodiments, the fragmented DNA sample is purified to a predetermined size that defines a spatial window that sets the resolution level for analysis. To the ends of the fragmented DNA are attached a short synthetic DNA adaptor that comprises an appropriate cohesive overhang to facilitate cloning the adaptor-ligated sample DNA into a suitable vector. The adaptor incorporates a recognition site for a suitable type IIS, type IIG or type III restriction endonuclease (for example: Mme I, NmeA III, CstM I, EcoP15 I, Pst II, Hpy790545P, or their preferred functional equivalent) in an orientation such that digestion of a library of insert-bearing plasmids with an aforementioned restriction endonuclease enzyme, cleaves the DNA inserts at a useful and defined distance from each insert terminus causing the release of the intervening sequence to yield a pair of Genomic Variation Tags (GVTs) that are attached to the vector. The newly linearized vector-GVT complexes are re-circularized by ligating the GVTs together to produce GVT-pairs that represent the two terminal regions of the original target DNA insert. Transfection of the circularized recombinant plasmids into host cells yield a primary GVT-pair library comprising individual plasmid clones each carrying a GVT-pair. The primary library is amplified and the purified plasmids are digested with a second restriction endonuclease that cuts at sites flanking the GVT pairs to release it from the plasmid vector. The released GVT-pairs are purified, oligomerized to a suitable size and are subcloned into a suitable vector for efficient high-throughput DNA sequence determination of the oligomerized GVT-pairs. When the sequence of individual GVTs of a GVT-pair are aligned computationally onto a reference sequence, any discordance with either their expected identity, separation distance or orientation with those aligned on the reference signals the presence of one or more fine structural differences between target and reference nucleic acids in the region spanned by the GVT-pair. Thus, the tabulated sequences of a plurality GVT-pairs constitute a detail genomic profile of the target nucleic acid population in respect to the reference sequence. These and other aspects of the invention will become evident upon reference to the following detailed description. In addition, various references (including patents, patent applications and journal articles) are identified below and are incorporated by reference herein.

Useful utilities offered by the present invention include but are not limited to the rapid construction of high-resolution genomic maps that can be used to: (1) Identify fine-scale-variations of the genome that contribute to human diversity and might be causal to disease, disease progression or disease susceptibility and other observed traits for use as diagnostics or as targets for therapeutic intervention; (2) Enable the design and creation of oligonucleotide microarray or other assay methods for rapid and massively parallel interrogation of fine-structural-variants in DNA samples for medical diagnosis, genotyping, and other such useful applications; (3) Facilitate accurate and rapid DNA assembly from whole genome or shotgun DNA sequencing approaches; (4) Identify fine-structural-variations of RNA transcripts resulting from differential RNA processing to aid genomic annotation, functional genomic studies, and potential disease diagnosis; (5) Create genomic profiles to facilitate comparative genomics and phylogenic studies and to aid differential identification of closely related organisms; and (6) Create genomic profiles of related strains, race, biotypes, variants, breeds or species to identify genomic elements that might be causal to any observable phenotypes of academic, medical or of commercial interest.

DETAILED DESCRIPTION OF THE PREFERRED EMBODIMENTS

The following methods provide background for the practice of the present invention and extends and combines aspects of the prior art to yield the novel and improved methods described and for the utilities indicated.

1. Fosmid Paired-End Mapping

Tuzun et al. (*Nat Genet* 37:727 (2005)) described the method of fosmid paired-end mapping where pairs of short sequence tags, separated by approximately 40 kb, were generated by terminal-end-sequencing of random ~40 kb genomic inserts derived from Human fosmid genomic libraries. Following alignment of tag-pairs to a reference genomic assembly, structural variations within the target DNA spanned by the tag-pairs were identified by discordance of expected marker separation distance and/or orientation with those aligned on a reference sequence. The method outlined by Tuzan et al. relied on fosmid packaging to produce tag pairs of ~40 kb (experimentally, the actually fragments range from 32 to 48 kb, <3 standard deviations from the mean, 39.9+/−2.76 kb) separation distance on genomic DNA. The authors did not teach or disclose other methods to create tag-pairs, to create tag-pairs of different spacing to change the spatial resolution of analysis, to improve the homogeneity of the inert lengths in their library, nor did they teach or disclose methods to produce other types of sequence tag-pairs such as those of the present invention that can demarcate genomic positions based on the location and/or separation distance between pairs of adjacent endonculease cleavage sites.

Many types of fine-structural-variations are not resolved by the ~40 kb resolution window fixed by the fosmid-paired end mapping approach. Fosmid paired-end mapping has further limitations. Fosmid vectors propagate in host cells at very low copy numbers, a property used to minimize potential recombination, rearrangement and other artifacts encountered during the propagation of certain genomic sequences in a bacterial host. Despite the current use of amplifiable versions of fosmid vectors (Szybalski U.S. Pat. No. 5,874,259) terminal sequencing of fosmid clones to generate tags still has very poor economy due to low DNA yield when compared to conventional plasmids, making high-throughput automated template production and sequencing difficult to maintain. Furthermore, two separate sequence reactions are required to generate a tag-pair sequence from a single fosmid DNA template, thereby reducing the economy further. The present invention overcomes these limitations through: (1) The ability to produce GVT-pairs whereby the spacing of tag-pair members on the target DNA can be engineered from 50 bp or less to several hundreds of kilo by or more to tailor detection resolution to suit the analysis of different types of nucleic acids and to suit any given experimental design; (2) Considerably more accurate and uniform spacing between tag-pair members for greater analytical precision; (3) The ability to produce genomic tag-pairs based on other criteria besides separation distance, such as the creation of tag-pairs based the location and/or the relative separation distance of adjacent endonuclease sites for improved interrogation of the target nucleic acid sample; and (4) Oligomerization of GVT-pairs and subcloning the GVT-pair oligomers into a vector optimized for high-throughput DNA sequencing to reduce operational cost, thereby enabling the present invention for use in broad population and cohort studies.

2. Methods for the Generation of Genomic Tags

A variety of DNA-based fingerprinting approaches have been described in the art to characterize and to compare genomes (Schloter et al. *Microbiol Rev* 24:647, (2000); Kozdroj and van Elsas *J Microbiol Meth* 43:197, (2001); Bouillard et al. *Genome Res* 11:1453, (2001); Wimmer et al. *Genes Chromosomes Cancer* 33:285, (2002)). All these approaches employed some combinations of restriction digestion of the target DNA, PCR amplification, or gel electrophoretic separation. In common, these approaches are laboriously encumbered by the need to extract candidate DNA fragments from gels for DNA sequencing. A step forward was the recent work of Dunn et al. where they described a method using the type IIS/type IIG restriction endonuclease, Mme I, to generate "Genomic Signature Tags" (GSTs) for analyzing genomic DNA (Dunn et al. *Genome Research*, 12:1756 (2002)). GSTs were generated by ligation of adaptors bearing a Mme I recognition site to genomic DNA fragments that were initially created by an initial digestion of the target DNA with a type II restriction enzyme followed by a second digestion with a frequent cutting tagging enzyme. Digestion of the adaptor ligated DNA with Mme I created a 21-bp tag (GST) with a fixed position in the DNA relative to the sites recognized by the initial restriction enzyme digestions. Following amplification by PCR, purified GSTs were oligomerized for cloning and sequencing. The identity of the tags and their relative abundance were used to create a high-resolution "GST sequence profile" of genomic DNA that can be used to identify and quantify the genome of origin within a given complex DNA isolate. Using *Yersinia pestis* as a model system, Dunn et al. were able to define areas in a relatively simple genome that might have undergone changes that added or deleted restriction sites. However, the method of Dunn et al. has limited utility in complex genomes such as that of man, where many structural variations are not revealed by the simple gain or lost of a site for a small number of restriction endonucleases under investigation. Furthermore, the number of GSTs required to cover a large genome or to analyze multiple samples for even one restriction site is prohibitive. In contrast to the method of Dunn et al, the GVT-pairs of the present invention provide the economy and the analytical power to profile complex genomes or to extend analysis to multiple DNA samples.

Versions of a method known as Serial Analysis of Gene Expression (SAGE), first described by Velculesu et al. (*Science* 270:484 (1995) and Kinzler et al. (U.S. Pat. No. 5,695,937), also made use of a type IIS or a type IIG restriction endonuclease to generate DNA tags (Saha et al. *Nat Biotechnol* 20:508 (2002); Ng et al. *Nat Methods* 2:105 (2005); Wei et al. *Proc Natl Acad Sci USA* 101:11701 (2004)). The so termed "SAGE tags" were generated from cDNA templates to provide an assessment of the complexity and relative abundance of cDNA species in a biological sample. Later versions of the SAGE approach referred to as "LongSAGE" made use of Mme I digestion to create tags of 21-bp in length to tag mRNA transcripts (Saha et al. *Nat Biotechnol* 20:508, (2002)). The most current refinement termed "SuperSAGE" made use of the type III restriction endonuclease, EcoP15 I, to produce a longer tag of 26-bp for improved mRNA assignment to the genome (Matsumura et al. *Proc Acad Sci USA* 100:15718-15723, (2003)). Although the present invention also makes use of type IIS, type IIG or type III restriction endonucleases to generate sequence tags, the resulting GVT-pairs of the present invention are fundamentally distinct from the aforementioned SAGE and GST tags by methods of production as well as by improved informational content. The use of pairs of linked tags offers a marked improvement in efficiency and analytical power over the use of unlinked tags for the generation of high-resolution physical maps that are particularly useful for characterizing novel genomes or annotating genomes and DNA samples for fine-structural-variations.

The recent work of Ng et al. (*Nat Methods* 2:105 (2005)) described a further development of the SAGE method. The investigators made use of a method pioneered by Collins and Weissman (*Proc Nail Acad Sci USA* 81:6812 (1984)) where circularization of DNA fragments, also referred to as intra-molecular DNA ligation, was employed to link distal DNA segments together into a vector to produce the so termed "genomic jumping libraries" (Collins et al. *Science* 235:2046 (1987)). Ng et al. circularized individual cDNAs to link their 5'- and 3'-derived SAGE tags together to produce "Paired-End Ditags" (PETs), which are then oligomerized to facilitate efficient sequencing. PETs are useful for genomic annotation by the identification of transcription start sites and polyadenylation sites of transcription units to set gene boundaries and to aid the identification of their flanking regulatory sequences. While the production the GVT-pairs of the present invention and the production of PETs by the method of Ng et al. both rely on intra-molecular ligation to achieve linkage of DNA markers, only the GVT-pairs of the present invention integrate accurate physical distance and other useful information between DNA markers thereby making GVT-pairs useful for detailed genomic structural analysis. Ng et al. did not teach methods to create tag-pairs of defined spatial spacing or of other criteria, nor did they describe how structural variations such as those that arise from mRNA processing or fine-structural-variations in the genome can be derived using their approach.

3. Multiplex Sequencing Vector

As used herein, the term multiplex sequencing vector refers to a plasmid vector optimized for high-throughput Sanger dideoxy sequencing that has the capacity to carry two or more independent inserts resulting in a plurality of sequencing reads from a single template, thereby enjoying cost saving through the economical use of materials.

The art as it is generally practiced is that one plasmid vector propagates a single DNA insert. Typical of such a configuration, a plasmid template can produce two sequencing reads from each of the two vector primer-binding sites flanking the DNA insert. Mead and Godiska (U.S. Pat. No. 6,709,861) described a "multiplex cloning vector" whereby DNA inserts are cloned into dispersed sites of a cloning vector, thereby allowing insert sequences to be subsequently sequenced either simultaneously in a single DNA sequencing reaction, or in parallel reactions using the same template preparation.

The multiplex cloning vector described by Mead and Godiska is available commercially as pLEXX-AK (Lucigen Corporation, Middleton, Wis.), and it is the principal component of the CLONEPLEX™ library construction system. Plasmid vector, pLEXX-AK, is provided by the vendor as two dephosphorylated blunt-ended vector DNA segments. Each vector segment carries a separate drug selectable marker and a pair of sequencing primer-binding sites for DNA sequencing. The vector system was promoted to reduce material cost for high throughput sequencing applications. In actual practice, the major high throughput application for DNA sequencing is shotgun genomic sequencing to which the pLEXX-AK vector system is not particularly well suited. In principle, the addition of phosphorylated blunt-end DNA inserts to a ligation reaction containing the two dephosphorylated pLEXX-AK vector segments would produce a configuration where a DNA insert is ligated between each of the two vector segments to yield a functional circular molecule. In practice, a complex milieu of ligation products is actually produced, in which only a small portion of the products comprises the desired circular molecule whereby a single DNA insert is ligated between the two different vector segments. While drug resistant markers on each of the two vector segments allow the selection of the productive species from the milieu, the system is inherently inefficient due to random undirected blunt-end ligation of the constituent vector and insert fragments. A large proportion of the input DNA inserts are expended in non-productive ligation events and a relatively large amount of starting DNA is needed to offset the lost. Most critically, the absolute requirement for phosphorylated blunt-end DNA inserts for cloning into the two sites of pLEXX-AK places a severe constraint on applications where sequence continuity of the original DNA inserts is critical such as for the construction of genomic DNA libraries for shotgun sequencing. For this application, any genomic insert ligated to other genomic insert (the so called chimeric inserts) during library construction would severely undermine the subsequent genomic assembly constructed from the sequence data. Furthermore, despite the claim by the investigators that their approach could be extended to the construction of vectors bearing independent inserts at three or more dispersed sites on the vector to increase efficiency further, the reliance on blunt-end ligation and the need for multiple selection markers for retention of each vector segments makes the claim impractical to carry out in practice.

The present invention overcomes the aforementioned limitations of the approach described by Mead and Godiska (U.S. Pat. No. 6,709,861) for the construction of a multiplex sequencing vector and provides improved materials, methods, and strategies for directed assembly of ever-more complex DNA molecules, vector and vector components to facilitate efficient multiplex DNA sequencing and other applications. Specifically, the present invention describes a modular vector system whereby individual vector components are flanked by unique type IIS restriction enzyme sites to create asymmetric cohesive ends to direct the ordered assembly of the vector modules and intervening DNA elements to any desired configuration at high efficiency to acquire new functionalities. A plasmid derived from the present invention, pSLGVT-3, is a high number copy plasmid optimized for high-throughput DNA sequencing and can carry at least two independent inserts to enable four separate sequencing reads from a single template. A second plasmid, pSLGVT-2, is a low copy number plasmid variant of pSLGVT-3 that is optimized for propagation of long DNA segments or those inserts that might be difficult to propagate in a microbial host without rearrangement or recombination. The two independent cloning sites on pSLGVT-2 and pSLGVT-3 make use of unique sets of non asymmetric complementary cohesive ends for the ordered and specific ligation of independent inserts at the two cloning sites, thereby abrogating the need for blunt-end cloning and the requirement for phosphorylated DNA inserts the principle cause for the generation of insert chimeras during library construction. Another distinguishing feature pSLGVT-series of plasmids from pLEXX-AK of Mead and Godiska (U.S. Pat. No. 6,709,861) is the use of the plasmid replicon as a biological selection of correct plasmid assembly, thereby reducing the material size of the vectors to increase the insert size carrying capacity. If required, the modular construction of the pSLGVT vectors and the use of asymmetric cohesive ends between vector modules permit rapid reconfiguration of the vector system to carry three or more independent DNA inserts.

1. Preparation and Fragmentation of Nucleic Acids for Production of GVT-Pairs

As described herein, the present invention provides methods to produce high-resolution genomic maps that can be used to characterize unknown genomes or to identify fine-structural-variations between target populations of nucleic acids and a reference sequence. Target nucleic acids suitable for analysis include but are not limited to: Genomic DNA of eukaryotic and prokaryotic organisms, microbial DNA, plastid DNA, plasmid and phagemid DNA, viral DNA and RNA, complementary DNA (cDNA) derived from ribonucleic (RNA), and DNA produced by in vitro amplification such as by PCR among others. Methods for DNA isolation from aforementioned sources, synthesis of cDNA from RNA and for the amplification of nucleic acids are known to those skilled in the art.

For certain embodiments of the present invention, the genomic distance spanned by the GVT-pair determines the resolution level for analysis. The smaller the spacing between GVTs, the higher is the resulting spatial resolution for mapping and for detecting fine-structural-variations in a target population of nucleic acid. Large GVT spacing requires fewer GVT-pairs to cover a DNA sample of a given complexity but with a concomitant decrease in spatial resolution. For identification of mRNA processing variants, GVT spacing of 50 or 100 bp offers sufficient resolution levels to detect most products of alternative splicing in cDNA populations. For human whole genome surveys, GVT spacing of 10, 25, 50 or 100 kb offers a productive compromise between resolution and economy. The functional tradeoff between GVT spacing, the resolution level required to detect different types of DNA structural variations, and the number of GVT-pairs needed to cover a given sequence complexity to a required depth can be modeled computationally to derive an optimal experimental design for a given application.

As described above, the material length of target DNA insert used for the construction of the GVT-pairs governs the separation distance between resident GVTs of a GVT-pair, thus setting the resolution level for the analysis. Methods to create and to purify a near size-homogeneous population of fragmented nucleic acids have been described in the art. Fragmentation of target DNA to a desired length can be accomplished enzymatically under conditions of partial or complete digestion with a variety of restriction endonucleases. The use of restriction endonuclease with recognition sites of six or greater base pairs are useful to produce longer DNA fragments. The use of frequent cutting type II endonucleases such as Mbo I, Hae III, and the like, which cut DNA once on average every 256-bp, is known in the art for producing varied sizes of DNA fragments by partial digestion. The use of restriction endonuclease CviJ I under relaxed conditions, which cleaves DNA at GC dinucleotide positions (Fitzgerald et al. *Nucleic Acids Res* 20:3753 (1992)), is particularly useful under partial digestion conditions to produce a useful continuum of DNA fragment sizes. In some embodiments, randomly generated DNA fragments are useful. The method for random generation of DNA fragments include: (1) Digestion with bovine pancreatic deoxyribonucleic acid nuclease I (DNase I), which makes random double-strand cleavages in DNA in the presence of manganese ions (Melgar and Goldwait *J Biol Chem* 243:4409 (1968); Heffron et al. *Proc Natl Acad Sci USA* 75:6012 (1978)); (2) Physical shearing (Shriefer et al. *Nucleic Acids Res* 18:7455 (1990)); and (3) Sonication (Deininger *Anal Biochem* 129:216 (1983)). Randomly fragmented DNA fragments of desired lengths can also be generated through the use of random primers during cDNA synthesis or by the use of PCR, alone or in combination with other fragmentation methods described.

Conditions for partial enzymatic digestion are determined empirically, varying one or more parameters of reaction volume, enzyme concentration, and enzyme to substrate ratio, incubation time or temperatures. For high-resolution analysis requiring a GVT separation of ~5 kb or less, fragmentation methods that are not sequence dependent is preferred. Bovine pancreatic DNase I makes random double-strand cleavages in DNA in the presence of manganese ions (Melgar and Goldwait *J Biol Chem* 243:4409 (1968); Heffron et al. *Proc Natl Acad Sci USA* 75:6012)) and can be used for this purpose. Likewise, DNA fragmentation by mechanical means such as sonication, or the selective application of shear forces can also be used. The HydroShear instrument (Genomic Solutions Inc, Ann Arbor, Mich.) is particularly useful for generating random DNA fragments of a defined size range. Random DNA fragments can also be generated through the use of random primers during cDNA synthesis or by use of PCR, alone or in combination with the other fragmentation methods described. The progress of fragmentation to yield the desired length product is most easily monitored by gel electrophoresis. Following generation of a suitable DNA size-distribution, $T_4$ DNA polymerase is used to repair or to make blunt the DNA ends in preparation for blunt-end ligation to GVT-adaptors for the production of the GVT-pairs of the present invention. In cases where DNA is fragmented by partial or complete digestion with one or more endonucleases leaving cohesive ends, repair is not necessary but the design of the GVT-adaptor will need to accommodate the cohesive ends generated by the fragmentation enzyme. Since ligation of inserts to other inserts destroys the co-linearity of the target DNA and undermines the construction of the genomic map, the insert DNA's 5' phosphate groups are removed by a phosphatase to prevent the ligation of insert DNA to other insert DNA during ligation to GVT-adaptors.

2. Size Fractionation and Purification of Size-Selected DNA

For certain embodiments, dephosphorylated DNA inserts are fractionated by gel electrophoresis and are purified to yield DNA inserts of a desired size. Acrylamide gels are best used for fractionation of DNA from 50 bp to 1 kb. For fragment sizes of ~250 bp to 20 kb, 0.4% to 3% agarose gels are suitable. Pulsed field gel electrophoresis is suitable for fractionating DNA from ~10 kb to several hundreds of kb in size. These procedures are described in references therein (Rickwood and Hames (Eds), *Gel electrophoresis of nucleic acids: A practical approach* (Oxford University Press, New York, 1990); Hamelin and Yelle *Appl Theor Electrophor* 1:225 (1990); Birren and Lai *Pulse field electrophoresis: A practical guide* (Academic Press, San Diego, 1993)). DNA is sized with the use of suitable size markers electrophoresed in parallel with the sample and are visualized by staining. Gel slices containing DNA of a desired size are excised with a scalpel, where after the DNA is recovered from the gel matrix by electro-elution or by enzymatic or chemical degradation of the gel matrix. The recovered DNA fragments for analysis should be near homogeneous in size. Gel systems and electrophoretic conditions for maximizing separation resolution are known in the art. Two or more cycles of gel electrophoresis are used to obtain greater sample size homogeneity. Sample with size variance of more than 2.5% from the mean length may contribute to unacceptable noise for use by the present invention.

3. Design of GVT-Adaptor and Ligation to Target DNA

Those skilled in the art would realize the existence of a plurality of GVT-adaptor designs suitable for use in the present invention. In sum, a suitable GVT-adaptor comprises the following material properties: (1) A short top strand and a short bottom strand of 5' phosphylated oligonucleotides of unequal lengths capable of stable complementary base-pairing to yield a two strand structure; (2) One end of the GVT-adaptor has a short non palindromic single strand protrusion that can ligate to a vector having the complementary sequence; (3) The other adaptor end has a blunt-end structure or other suitable end structures to enable efficient ligation to dephosphylated target DNA fragments; (4) The end of the adaptor that flank target DNA bears a suitable type IIS, type IIG or type III restriction endonuclease recognition site in an orientation such that the site directs cleavage at a fixed and useful distance on the target DNA to produce the GVT; and (5) Adjacent or overlapping the type IIS, type IIG or type III enzyme recognition site is a second restriction endonuclease site for excising the created GVT-pair from the vector. Illustrative examples of suitable GVT adaptors are depicted below (examples Nos 1-4).

Example No 1

GVT (Mme I)-Adaptor for Blunt Ligation to Dephosphorylated Target DNA

```
5'-pGACACAGAGGA TCCAAC        (Seq ID No: 1)
      GTCTCCT AGGTTGp -5'     (Seq ID No: 2)
              Mme I
```

The sequence 5' pGACA-3' of illustrative example No 1 (Seq ID No 1), is a cohesive end for sub cloning adaptor-ligated DNA insert into a vector with a pair of protruding 5'-TGTC-3' sequence. The cohesive end is non-palindromic to prevent the formation of adaptor dimers and multimers of DNA bearing ligated adaptor and prevents the creation of insert-less vectors. The 5'-CAGAGGA-3' sequence of Seq ID No 1 and its reverse complement, 5'-TCCTCTG-3', on Seq ID No 2 depict a short sequence capable of stable complementary base pairing to aid the formation of a functional two-strand adaptor. The 5'-TCCAAC-3' sequence of Seq ID No 1 and its reverse complement, 5'-GTTGGA-3', on Seq ID No 2 is the recognition site for the type IIS endonuclease, Mme I (Boyd et al. *Nucleic Acids Res* 14:5255 (1986)). Mme I cleaves DNA 20 bp downstream (that is in a 5' to 3' direction) from its 5'-TCCAAC-3' recognition site and 18 bp upstream (that is in a 3' to 5' direction) from its reverse complement on the opposite strand to yield a 20-bp GVT, with 2-bp a protruding 3'-overhang. Overlapping the Mme I recognition site is the recognition site for BamH I, 5'-GGATTC-3'. BamH I cleavage serves to release of the created GVT-pair from the vector. The BamH I site overlaps the Mme I site in order to minimize extraneous adaptor sequences for greater economy during sequence determination of the oligomerized GVT-pairs. To achieve the same end in other adaptor designs, an overlapping BspT I site can be used for the excision of GVT-pairs that are created by CstM I digestion. Similarly, Kas I can be used to excised GVT-pair created through the digestion with NmeA III.

Example No 2

GVT (Mme I)-Adaptor Ligation to Dephosphorylated Target DNA Digested with Xba I

```
5'-pGACACAGAGGA TCCAAC            (Seq ID No: 1)
       GTCTCCT AGGTTGGATCp -5'    (Seq ID No: 3)
               Mme I
```

The salient features of the GVT (Mme O-adaptor of illustrative example No. 2 is identical to those of illustrative example No 1, with the added incorporation of a 5'-pCTAG-3' overhang (Seq ID No 3) to direct ligation of the adaptor to Xba I digested dephosphorylated target DNA fragments. Those that are skilled in the art would realize that the adaptor of example No 2 is but one variant. There exist other functional adaptor variants created through the incorporation of a suitable overhang that ligate to target DNA digested with other restriction endonucleases to suit different experimental designs.

Example No 3

GVT (EcoP15 I)-Adaptor for Blunt Ligation to Dephosphorylated Target DNA

```
5'-pGACACAGACTG CAGCAG            (Seq ID No: 4)
       GTCTGAC GTCGTCp -5'        (Seq ID No: 5)
               EcoP15 I
```

Example No 4

GVT (EcoP 15 I)-Adaptor for Cohesive-End Ligation to Dephosphorylated Target DNA Digested with Xba I

```
5'-pGACACAGACTG CAGCAG            (Seq ID No: 4)
       GTCTGAC GTCGTCGATCp -5'    (Seq ID No: 6)
               EcoP15 I
```

Illustrative examples No 3 and 4 depict adaptor designs that utilize the type III restriction endonuclease, EcoP15 I, to produce a 27-bp GVT. A restriction endonuclease site for Pst I (5'-CTGCAG-3') for excision of the GVT-pair overlaps the EcoP15 I site (5'-CAGCAG-3'). Overlapping the Pst I site with the EcoP15 I site minimizes extraneous adaptor sequence within GVT-pair for greater economy during sequencing. The adaptor of illustrative example No 4 incorporates a Xba I cohesive end to direct ligation of adaptor to dephosphorylated Xba I digested target DNA fragments. Those that are skilled in the art would realize that the adaptor of example No 4 is but one variant. There exist other functional adaptor variants created through the incorporation of a suitable overhang that ligate to target DNA digested with other restriction endonucleases to suit different experimental designs.

The illustrative GVT-adaptors of illustrative example Nos 1 and 2 can either produce an 18 bp or 20-bp long GVT by digestion with Mme I. An 18-bp GVT is produce when $T_4$ DNA polymerase is used to remove the 3'-overhang created from Mme I cleavage prior to blunt-end ligation of the linked GVTs to generate a 36-bp GVT-pair. A 20-bp GVT results when an adaptor having 16-fold degenerate 5'-overhangs, compatible with all possible two-base 3' overhangs generated from Mme I digestion, is used to ligate the GVTs together to produce the GVT-pair. In contrast to Mme I, EcoP 15 I cleavage creates 2-bp 3' recessed ends, which is extended by DNA polymerase to yield a 27-bp blunt-ended GVT, from which a 54-bp GVT-pair is created by blunt-end ligation.

Any type IIS or type IIG restriction endonucleases that recognize an uninterrupted nucleotide sequence and cleaves at least ten base pairs distant from its recognition site are suitable for use in the generation of GVT. These enzymes include: BceA I, Bpm I, BpuE I, Bsg I, BsmF I, BstV1 I, Eco57 I, Eco57M I, Gsu I, CstM I, NmeA III, and Mme I. Of these, Mme I, NmeA III, or CstM I are preferred for use by the present invention since their cleavage site is the most distant from its DNA recognition site among the type IIS endonucleases described to date, thereby producing a GVT of the longest length. It is anticipated that other type IIS or type IIG endonucleases with longer defined cleavage distance from its recognition site will be discovered in the future and can be used by the present invention. For reviews of the type IIS and JIG restriction endonucleases see Sistla and Rao (*Critical Rev Biochem Biol* 39:1, (2004)) and Bujnick (*Acta Biochimica Polonica* 48:935, (2001)).

The type III restriction endonucleases were initially described to require two inverted asymmetric recognition sites and that cleavage in vivo occurs distal to only one of the two pairs of inverted recognition sites chosen at random. For review, see Sistla and Rao *Critical Rev Biochem Biol* 39:1, (2004)) and Bujnick (Acta Biochimica Polonica 48:935, (2001)). Such properties are not useful by the present invention. However, characterization of the prototype type III enzyme, EcoP 15 I, indicated that recombinant or the purified native enzyme when used at two to three-fold higher concentration and in the presence of potassium ions is capable of promiscuous cleavage at single sites in vitro (Mucke et al. *J Mol Biol* 312:287, (2001); Peakman et al. *J Mol Biol* 333:321, (2003); Raghavendra and Rao *Nucleic Acids Res* 32:5703, (2004); Sistla and Rao Critical Rev *Biochem Biol* 39:1, (2004)). This newly described property of EcoP15 I was exploited to produce SAGE tags from cDNA (Matsumura et al. *Proc Acad Natl Sci USA* 100:15718, (2003)). The EcoP15 I enzyme is commercially available (New England Biolabs, Ipswich, Mass.) and is used by the present invention to produce a 27-bp GVT and a subsequent 54-bp GVT-pair. Other type III endonucleases that cleave DNA at a useful distance from its recognition site can be used by the present invention.

Those of skill in the art know methods for ligation of adaptor to DNA insert and for general ligation of nucleic acid molecules. See, for example, Ausubel et al. (Eds.), *Short Protocols in Molecular Biology*, 3rd Ed, (John Wiley & Sons 1995). Typical ligation conditions for blunt-end ligation of adaptor to DNA insert call for a ~50 to 500-fold molar excess adaptor to target DNA, high $T_4$ ligase concentration, or the inclusion of a volume exclusion agent such as polyethylene glycol (Pheiffer and Zimmerman *Nucleic Acids Res* 11:7853 (1983); Zimmerman and Pheiffer, *Proc Natl Acad Sci USA* 80:5852 (1983); Harrison and Zimmerman *Nucleic Acids Res* 12:8235 (1984); Hayahi et al. *Nucleic Acids Res* 14:7617 (1986)). Ligation of adaptor to cohesive end target DNA requires ~5-fold molar excess. GVT-adaptor-ligated DNA inserts are passed through a ChromoSpin column (Clontech, Mountain View, Calif.) to remove excess adaptors before purification and size-selection by gel electrophoresis. To generate GVT-pairs by intra-molecular ligation, the purified products are ligated into one of several plasmid vectors described below.

4. Vector Construction for GVT-Pair Production

An aspect of the present invention provides general methods to produce cloning vectors that are capable to generate GVT-pairs by digestion of the insert with either a type IIS, type IIG or a type III endonuclease followed by intra-molecular ligation. A GVT-DNA cloning cassette comprising the material features depicted below is used to modify existing cloning vectors by ligation of the cassette into a suitable site.

Example 5

Illustrative Example of a GVT-DNA Cloning Cassette

```
5' AATTGGACAA (GAGACG) GAATAT (TCTAGA) ACGATA
        CCTGTT (CTCTGC) CGTATA (AGATCT) TGCTAT
   EcoR I     Esp3 I         Xba I
   (CGTCTC) CTGTCC                      SEQ NO ID: 7
   (GCAGAG) GACAGGTTAA 5'               SEQ NO ID: 8
   Esp3 I         EcoR I
```

The GVT-DNA cassette is produced synthetically from two complementary oligonucleotides (Seq ID No 7 and Seq ID No 8) annealed to form a double strand structure with terminal cohesive ends suitable for ligation into an existing vector. As an illustrative example, the DNA cassette above is shown with protruding cohesive ends for EcoR I for replacement of the multiple cloning site region of pSMART VC or pSMART-cDNA (Lucigen, Middleton, Wis.) to render these plasmid vectors capable to produce GVT-pairs in conjunction with the previously described GVT-adaptor ligated target DNA. A material feature of the DNA cloning cassette is an inverted pair of type IIS or type IIG endonuclease sites; Esp3 I in the illustrative example. Digestion of modified vector with Esp3 I creates a pair of non-palindromic overhangs (5'-TGTC-3') on the vector that ligate specifically to complementary overhangs (5'-GACA-3') extending from GVT-adaptor-ligated target DNA inserts. The non-rotational symmetry of the vector and insert overhangs essentially eliminates the creation of insert-less plasmids and plasmids bearing multiple copies of adaptor-ligated target DNAs, which would compromise the colinearity of the target DNA insert and the subsequent creation of the genomic profile. The DNA cassette also incorporates the restriction endonuclease site, Xba I, situated between the pairs of inverted Esp3 I sites. A "stuffer DNA" fragment of a suitable size cloned at the Xba I site enables the monitoring of Esp3 I digestion during vector preparation. The length of the stuffer DNA fragment is selected such that Esp3 I single-digested, double-digested and undigested vector species can be easily resolved by gel electrophoresis and only fragments from double digestion are purified for use.

Those that are skilled in the art would realize that as with the previously described examples of suitable GVT-adaptor, the DNA cloning cassette described above is but one of a plurality of functionally equivalent designs. For example, the Esp3 I sites in the DNA cassette can be substituted with those of other type IIS or type IIG endonucleases where DNA cleavage is distal from a contiguous recognition site. Suitable type IIS or type IIG enzymes include: Alw I, Alw26 I, AsuHP I, Bbv I, Bcc I, BseG I, BseMi I, BsmA I. BsmF I, BsoMA I, BspCN I, BspM I, BspP I, BspTN I, BstF5 I, BstV1 I, Fau I, Fok I, Hga I, Hph I, Lwe I, Ple I, Pps I, Sfa I, Smu I, TspDT I, TspGW I, Bbs I, BciV I, Bfi I, Bfu, I, Bmr I, Bpi I, Bpm I, BpuA I, BpuE I, Bsa I, Bse3D I, BseM I, BseR I, BseX I, Bsg I, BsmF I, Bso31 I, BsrD I, Eco31 I, Esp3 I, BstV2 I, Bve I, Eam1104 I, Eci I, Eco57 I, Eco57M I, Faq I, Gsu I, Ksp632 I, CstM I, Mme I, NmeA III, Taq II, Sap I, their isoschizomers and other examples described by Szybalski et al. (*Gene* 100: 13 (1991)). Prefer enzymes are those with six base pair or longer recognition sites, (for example: BspM I, Eco31 I, Esp3 I, Sap I and their isoschizomers) since the sites for these enzymes are less likely to occur in vector backbones and reduce the need for site-directed mutagenesis to eliminate these sites during vector construction. Also obvious to those that are skilled in the art are the precise sequences of the cohesive ends generated by the aforementioned enzymes can vary as long as they can form functional and specific base-pair with their intended ligation partners. The end structures on the DNA cassette can be modified to accommodate ligation of the cassette into the desired sites on preexisting vectors or to isolated vector components to create new vectors that can be used by the present invention.

The ability to propagate DNA segments stably in host cell is of critical importance for genomic analysis. Rearrangement or the lost of DNA segments containing AT- or GC-rich regions, repeats, hairpins, strong promoters, toxic genes and other problem sequences when propagated in host cell are of great concern for the study of fine-genomic-variations. DNA rearrangements and other cloning artifacts can be mistaken for structural variations in the target nucleic acid. Moreover, cloning bias can limit the size of inserts and can under-represent important regions of the genome from study. This problem was addressed recently by the development of fosmid and BAC vectors with conditional amplification systems (Szybalski U.S. Pat. No. 5,874,259) where propagation of DNA is kept at one to two copies per host cell until induced to higher levels for analysis. Improved stability of genomic inserts of 15 kb to over 100 kb was reported and conditional amplification vectors are now in routine use for genomics studies. Conditional amplification fosmid/BAC vectors such as pCC1FOS (Epicentre, Madison, Wis.) and pSMART VC (Lucigen, Middleton, Wis.) and their variants are suitable for use in GST-pair production of GVT-spacing from 10 kb to 200 kb. However, use of conventional low-copy plasmid vectors appeared to be sufficient for stable maintenance of large DNA fragments without the need of BAC, PAC or fosmid type vectors (Feng et al. *BioTechniques* 32:992, (2002); Tao and Zhang *Nucleic Acids Res* 26:4901, (1998)). The pSMART series of vectors offers low copy number propagation and has the added feature of having transcription terminators on the vector to reduce the potential effects of transcriptional interference, which might further improve DNA stability (Mead and Godiska U.S. Pat. No. 6,709,861). For GVT-pair production of GVT-spacing from 50 bp to 10 kb or more, a variety of established and widely used low copy plasmid-based vectors are suitable for modification to produce GVT-pairs, including: pBR322 (Bolivar et al. *Gene* 2:95, (1977)), and pACYC177 (Chang and Cohen *J Bacteriol* 134:1141, (1978)).

Vectors for GVT-pair production are produced by insertion of the GVT-DNA cassette into a suitable vector backbone at suitable cloning site. General methods for ligating nucleic acid molecules are known to those of skill in the art. See, for example, Ausubel et al. (Eds.), *Short Protocols in Molecular Biology*, 3$^{rd}$ Ed (John Wiley & Sons, New York, 1995). For use, the vector backbone must be rendered free of the recognition sites for: (1) The type II, IIS or type IIG restriction endonuclease used to generate the cohesive ends on the DNA cloning cassette for direct cloning the target DNA or the adaptor-ligated target DNA; (2) The type IIS, type IIG or type III endonuclease used to generate the GVT from the cloned target DNA insert; and (3) the enzyme used to excise the newly created GVT-pair from the plasmid. For the illustrative examples of a GVT-DNA cassette and GVT-adaptors, the vector backbone needs to be free of a specific combinations of Esp3 I, Eco31 I, CstM I, Mme I, NmeA III, Pst II, EcoP 15 I, BamH I, Pst I, BspT I or Kas I sites, with the actual requirement dictated on the precise configuration of GVT-DNA cassette and adaptor in use. If required, the vector backbone can be rendered free of those aforementioned sites by site directed mutagenesis employing standard methods. See, for example: McPherson (Ed), *Directed mutagenesis: A practical approach* (Oxford University Press, New York, 1991) and Lok (U.S. Pat. No. 6,730,500). Typically, a substantial portion of vector DNA can be altered by single base-pair change to eliminate unwanted restriction endonuclease recognition sites without undue effects on vector functionality. Within protein coding sequences, single nucleotide changes are targeted to the codon wobble positions to maintain native protein coding. Changes made elsewhere on the vector backbone would require functional validation before use.

5. GVT-Pair Production Vectors pSLGVT-1 and pSLGVT-2

Plasmids, pSLGVT-1 and pSLGVT-2, of the present invention are optimized and versatile vectors specifically designed to produce GVT and GVT-pairs employing Mme I or EcoP15 I, respectively. pSLGVT-1 and pSLGVT-2 are also free of CstM I and NmeA III sites and can be used to produce GVT and GVT-pairs employing these two enzymes in accordance to the methods of the present invention. The basic vector comprises two chemically synthesized DNA modules to provide the basic maintenance functions of drug selection and plasmid replication, respectively. Connecting the two DNA modules to yield a circular molecule are DNA cassettes that provides specific utilitarian functions to the basic plasmid backbone. The vector modules bear terminal unique type IIS restriction endonuclease sites that create unique asymmetric cohesive ends to allow rapid future reconfiguration of the vector components to add or substitute modules or DNA cassettes for new functionalities.

The first vector module comprises a modified P15A origin of replication. Plasmids bearing the P15A replicon propagate at a low number of approximately 15 copies per host cell (Sambrook et al. *Molecular Cloning: A Laboratory Manual*, 2$^{nd}$ ed. CSH Laboratory Press, Cold Spring Harbor, N.Y., (1989)), thereby optimizing the stability of cloned genomic inserts. In contrast, high copy number plasmids, such as the pUCs or pBluescript, may reach several thousand copies per cell. Two Mme I sites within the P15A replicon are each eliminated by a single nucleotide change to yield the "P15A-m replicon module" for the construction of plasmid pSLGVT-1. Mutation of these two sites is not expected to alter the secondary structure or the transcription of RNA II or RNA I required for the regulation of plasmid replication. The single EcoP15 I site in the P15A replicon is eliminated in the same fashion to yield the "P15A-e module" for the construction of plasmid pSLGVT-2. Both versions of the p15A modules are flanked at the RNA II promoter end of the module by a unique Bpi I site generating a 5' GTGA-overhang to facilitate ligation of DNA cassettes. For the same purpose, the replication fork end of the replication modules are flanked by a Faq I site generating a 5' TCTC-overhang.

The second vector module comprises a modified version of the Kan gene from transposon Tn903 conferring resistance to antibiotic Kanamycin (Grindley et al. *Proc Natl Acad Sci USA* 77:7176, (1980)). Taking advantage of the wobble position and conforming to the optimal codon usage in *E. coli* whenever it is possible, four Mme I sites along with two Nci I and Nsi I sites, and single sites for Esp3 I, Pst II, and Hind III are removed within the coding region of the Kan gene to yield the "Kan module". The Kan module is flanked at the Kan promoter end of the module by a unique Sap I site to generate a 5' TTG-overhang for DNA cassette ligation. The unique BspM I at the other end of the Kan module generates a 5' ACTG-overhang for the same purpose. Kanamycin drug selection is generally acknowledged to offer the best stability for the maintenance of plasmids bearing particularly long and/or difficult inserts and in many situations its use would also allow limited but convenient amplification of plasmid libraries in liquid cultures without undue clonal selection that can distort the composition of the plasmid library.

The core components of the pSLGVT series of plasmids are two DNA Cloning Cassettes, which provide specific insert cloning functionalities and serve to link the Kan module and the replicon modules together to yield a circular plasmid. Plasmids, pSLGVT-1, -2 and -3 have a common structure comprising the following material features on a circular map in the clockwise direction: (1) The Replicon Module; (2) DNA Cloning Cassette 1; (3) The Kan Module; and (4) DNA Cloning Cassette 2. Plasmid replication and the transcription of the Kan gene proceed in a clockwise direction. The structure of DNA Cloning Cassettes 1 and 2 is indicated below:

Example 6

DNA Cloning Cassette 1 and 2

```
DNA Cloning Cassette 1.
5'GAGA(T7>)GACAA(GAGACG)GCATCTCAGTAG(TCTAGA)AGTGCACGATAG
      (T7  )CTGTT(CTCTGC)CGTAGAGTCATC(AGATCT)TCACGTGCTATC
                        Esp3 I                Xba I
   (CGTCTC)CTGTC( T3)                                       SEQ ID NO: 9
   (GCAGAG)GACAG(<T3)CAA                                    SEQ ID NO: 10
   Esp 3 I
```

```
DNA Cloning Cassette 2.
5'GAGT(M13F>)CTGAT(GAGACC)CTAGCCTCTTGA(GTCGAC)CACTATACATCA
     (M13F )GACTA(CTCTGG)GATCGGAGAACT(CAGCTG)GTGATATGTAGT
           Eco31 I                  Sal I
(GGTCTC)CTCAG( M13R)                                SEQ ID NO: 11
(CCAGAG)GAGTC(<M13R)CACT                            SEQ ID NO: 12
 Eco31 I T7 sequencing primer: 5'-TAA TAC GAC TCA CTA TAG GG-3'    SEQ ID NO: 13

T3 sequencing primer: 5'-ATTAACCCTCACTAA AGG GA-3'        SEQ ID NO: 14

M13 F sequencing primer: 5'-CAC GAC GTT GTA AAA CGA C-3'  SEQ ID NO: 15

M13 R sequencing primer: 5'-GGA TAA CAA TTT CAC ACA GG-3' SEQ ID NO: 16
```

DNA Cloning Cassettes 1 is produced from two complementary chemical synthesized oligonucleotides annealed to form a double strand structure with two terminal asymmetric 5' protruding cohesive ends, 5'''-GAGA-3' and 5'-AAC-3', for directed ligation of the cassette to the 5 '-TCTC-3' overhangs of the replicon module (P15A-m or P15-e) and to the 5'-GTT-3' overhang of the Kan modules, respectively. The binding sites on the DNA cloning cassettes 1 and 2 for sequencing primers T7, T3, M13 forward and M13 reverse are shown. Those that are skilled in the art would know of other sequencing primer binding sites suitable for use by the present invention. A pair of inverted Esp3 I sites on DNA cloning cassette 1 produces a pair of 5'-TGTC-3' overhangs on the vector to receive the GVT-adaptor ligated target DNA for the product of GVT-pairs. A Xba I site is situated between the set of Esp3 I sites for cloning a stuffer DNA fragment to help monitor the progress of Esp3 I digestion in the preparation of the vector to receive GVT-adaptor ligated target DNA. Flanking the Esp3 I sites are primer-binding sites for the T7 and T3 sequencing primers. These primers sites are used to sequence portions of the target DNA insert for quality control of library construction. As will be described below and a later sector of this disclosure, a variant of the pSLGVT-plasmid series, pSLGVT-3, utilizes these primer sites for high-throughput multiplex DNA sequencing of oligomerized GVT-pairs.

DNA Cloning Cassettes 2 is produced from two complementary chemical synthesized oligonucleotides annealed to form a double strand structure with two terminal asymmetric 5' protruding cohesive ends, 5'-GAGT-3' and 5'-TCAC-3', for directed ligation of the cassette to the 5'-ACTC-3' overhangs of Kan module and to the 5'-GTGA-3' overhang of replicon module (P15A-m or P15-e), respectively. A pair of inverted Eco31 I sites on DNA cassette 2 produces a pair of 5'-TCAG-3' overhangs on the vector and provides alternate site to receive the GVT-adaptor ligated target DNA for the production of GVT-pairs. A Sal I site is situated between the set of Eco31 I sites for cloning a stuffer DNA fragment to help monitor the progress of Eco31 I digestion in preparation of the vector to receive target DNA. Flanking the Eco31 I sites are primer-binding sites for the M13 forward and M13 reverse sequencing primers. These primers sites are used to sequence portions of the target DNA insert for quality control of library construction. As will be described below and elsewhere in this disclosure, a variant of the pSLGVT-plasmid series, pSLGVT-3, utilizes these primer-binding sites for high-throughput multiplex DNA sequencing of oligomerized GVT-pairs.

Plasmid pSLGVT-1 is constructed by the two-part ligation strategy. The P15A-m replicon module is incubated with DNA Cloning Cassette 1. In a separate ligation reactions, the Kan module is incubated with DNA Cloning Cassette 2. After one-hour incubation the two ligation reactions are combined to assemble the desired circular product. Plasmid pSLGVT-2 is produced by a similar manner but with the P15A-e replicon module replacing the P15A-m replicon module in the initial ligation reaction.

An alternative route to the construction of pSLGVT-series of plasmids is through chemical synthesis whereby the plasmids are assembled from a series of chemically synthesized oligonucleotides.

Plasmid pSLGVT-3 of the present invention represents a novel approach for efficient construction of a family of multiplex DNA sequencing vectors for sequencing oligomerized GVT-pairs and other DNA segments. Plasmid pSLGVT-3 is constructed by replacing the P15A replicon module on the Bpi I-Fag I fragment of pSLGVT-2 with a fragment terminating with those sites containing the replicon derived from the pUC plasmid. The pUC replicon was derived from the low copy number ColE1 replicon where a single base mutation in the Ori combined with the deletion of the rop regulator resulted in increased plasmid copy number from ~20 copies to greater than a thousand copies per cell (Vieira and Messing *Gene* 19:259, (1982)). The high copy number of pSLGVT-3 would facilitate template preparation for high-throughput DNA sequencing of oligomerized GVT-pairs. A salient feature pSLGVT-3 is the aforementioned pairs of inverted type IIS restriction enzyme sites residing in DNA cassettes 1 and 2. Digestion of pSLGVT-3 with Esp3 I and Eco31 I creates two DNA vector segments with asymmetric cohesive ends for the targeted and directed ligation of two independent sets of oligomerized GVT-pair segments allowing four separate sequencing reads from each of the four primer-binding sites present in DNA cassettes 1 and 2. Conventional sequencing vectors typically carry one insert and can support only two sequencing reads.

6. GVT-Pair Production

As used herein, fosmid, BAC and other episomal elements are referred collectively as plasmids, the method described below for GVT-pair generation is based the previously described illustrative examples of the GVT-DNA cassettes and GVT-adaptors. In certain embodiments, target DNA for GVT-pair production are fragmented randomly by mechanical or enzymatic means to produce fragments of a desired size for GVT-pair production. In other embodiments, target DNA are digested to completion with one or more restriction endonucleases in separate reactions or in combination to cleave target DNA at specified sites to produce a population of DNA fragments for production of GVT-pairs as described in this disclosure. For target DNA digested with enzymes that create cohesive ends, the dephosphorylated insert DNA may be cloned directly into a site between a pair of type IIS or type IIG sites of a suitably modified vector without the need of an adaptor. In yet another embodiment, target DNA are digested to completion with one or more restriction endonucleases and are fractionated to a desired size for use in GVT-pair production.

Target DNA for GVT-production having "ragged" ends are repaired using $T_4$ DNA polymerase and are dephosphorylated to prevent self-ligation of inserts during ligation of insert to the GVT-adaptor. Likewise, target DNA bearing cohesive ends are dephosphorylated before ligation to a suitable GVT-adopter bearing complementary ends. GVT-adaptor ligated DNA are passed through an appropriate Chroma Spin column (Clontech, Mountain View, Calif.) to remove unligated adaptor before ligation of adaptor-ligated target DNA to a GVT production vector. In certain embodiments, target DNA are size-selected to a desired length by gel electrophoresis or by other means prior to ligation of inserts to GVT-adaptor and subsequent ligation into a GVT-production vector such as pSLGVT-1 and pSLGVT-2 described in the present invention.

Ligation conditions for optimizing inter-molecular ligation of a vector to an insert followed by intra-molecular ligation to yield a circular molecule have been described for DNA segments over a range of fragment lengths (Wang and Davidson *J Mol Biol* 19:469 (1966); Dugaiczyk et al. *J Mol Biol* 96:171 (1975); Collins and Weissman *Proc Natl Acad Sci USA* 81:6812 (1984)). General methods for ligating nucleic acid molecules, transfection into host cell and for construction of plasmid-based libraries are known to those that are skilled in the art. See, for example, Sambrook et al. *Molecular Cloning: A laboratory manual* $2^{nd}$ Ed (CSH press, New York, 1989); Ausubel et al. (Eds.), *Short Protocols in Molecular Biology*, $3^{rd}$ Ed (John Wiley & Sons, New York 1995); Birren et al. *Bacterial artificial chromosomes in genome analysis: A laboratory manual* (CSH Press, New York, 1999). Ligated DNA is introduced into host cells by electroporation or by transfection. The propagation of methylated target DNA such as genomic DNA or cDNA synthesized by certain protocols that make use of methylated nucleotide analogues requires host cell strains with inactive mcr and mrr alleles. Suitable host strains include: 10G (Lucigen, Middleton, Wis.); XL1-Blue MR and XL2Blue MRF' (Stratagene, La Jolla, Calif.). Electroporated or transfected cells are plated onto 10 cm diameter agar plates at a density of ~20,000 colonies per plate under the appropriate drug selection to yield the primary library. An alternative method is to grow the transfected cells in liquid culture while exercising care not to overgrow cells to encourage clonal selection. The total number of clones under culture should reflect the number of GVT-pairs required by the study design. Cells are harvested and the plasmids isolated for the subsequent step described below.

As a general procedure, purified plasmids bearing target DNA insert are digested with either Mme I, CstM I, NmeA III, or EcoP15 I (New England Biolabs, Ipswich, Mass.) to generate the GVT in accordance with the experimental design. The ends of the newly created GVTs are repaired with $T_4$ DNA polymerase to render the digested ends blunt. Linearized plasmids with the newly created GVTs attached are purified away from the excised remnant of the intervening inserts by gel electrophoresis and the purified products are circularized by blunt-end ligation to yield the primary GVT-pair library. An alternative method for recircularizing the plasmids that avoids the need to repair DNA ends makes use of an adaptor bearing all 16-fold two-base pair degenerate 3'-overhangs or 5'-overhangs produced by Mme I, CstM I, NmeA III, or EcoP15 I digestion, respectively. The method would increase the length GVT produced by Mme I digestion from 18-bp to 20-bp but would not increase the length of EcoP15 I produced GVTs since EcoP15 I digestion creates 2-bp 3'-recessed ends that are filled in during repair by $T_4$ DNA polymerase prior to plasmid recircularization to the generate the GVT-pair. The use of an adaptor to recircularize the plasmid would increase the overall unit length of the resulting GVT-pairs with extraneous sequences with a resulting negative impact on sequencing economy of the oligomerized GVT-pairs.

Circularized plasmids are introduced into host cells and plated at a density of ~20,000 colonies per 10 cm plate or grown in liquid culture under selection to yield the primary GVT-pair library. Purified plasmids from the primary GVT-pair library are digestion with an enzyme that cleaves both sides of the GVT-pairs to excise the GVT-pair from the plasmid. In the illustrated examples of the GVT-adaptors used for library construction, BamH I or Pst I are used to excise the GVT-pairs from the Mme I or EcoP15 I generated GVT-pair libraries, respectively. Using a similar adaptor design, the enzymes BspT I or Kas I can be used to excise GVT-pairs from CstM I or NmeA III generated GVT-pair libraries, respectively. The general structure of an excised GVT-pair generated by either Mme I or EcoP15 I digestion followed by blunt-end ligation is shown below:

Example 7

Structure of a GVT-Pair Monomer Generated by Mme I Digestion, Intramolecular Ligation and Excision by BamH I Digestion

```
5' pGATCCAAC-18N-18N-GTTG         SEQ ID NO: 17
       GTTG-18N-18N-CAACCTAGp     SEQ ID NO: 18
       Mme I           Mme I
```

"18N-18N" represents the two juxtaposed 18-bp GVTs of a GVT-pair created from target DNA digested with Mme I. The pair of Mme I recognition sites on the monomer is underlined. The remaining portions of the 52-bp monomer, including the underlined Mme I sites, comprise a common "framework". The 52-bp GVT-pair monomer is separated by electrophoresis on a 5% polyacrylamide gel and is purified and oligomerized for sequencing.

Example 8

Structure of GVT-Pair Monomer Generated EcoP15 I Digestion, Intramolecular Ligation and Excision by Pst I Digestion

```
5' pGCAG-27N-27N-CTGCTGCA         SEQ ID NO: 19
   ACGTCGTC-27N-27N-GACGp 5'      SEQ ID NO: 20
     EcoP15 1         EcoP15 I
```

"27N-27N" represents the two juxtaposed 27-bp GVTs of a GVT-pair created from target DNA digested with EcoP15 I. The pair of EcoP15 I recognition sites on the monomer is underlined. The remaining portions of the 70-bp monomer, including the underlined EcoP15 I sites, comprise a common "framework." The 70-bp GVT-pair monomer is separated by electrophoresis on a 5% polyacrylamide gel and is purified and oligomerized for sequencing.

7. Production of Oligomerized GVT-Pair Monomers for Efficient DNA Sequencing

DNA sequence tags are typically oligomerized and cloned into a sequence vector as an extended oligomer for economic use DNA sequencing resources. The present invention provides efficient methods to create oligomers of DNA tags and assemble the oligiomerized DNA segments into an improved sequencing vector. Typically, DNA sequence tag monomers are constructed with termini bearing symmetric cohesive ends such as BamH I or Pst I in the examples shown. However, the commonly used procedures for producing and cloning oligomerized sequence tag monomers are inherently inefficient due the creation of unproductive circular products during the oligomerization reaction and during the ligation of the insert into vector. As described herein, a novel and preferred method to produce and to clone oligomerized sequence tags is outlined below. The improved procedure makes use of an "initiator adaptor", which can initiate oligomerization of monomers and allows cloning the oligomeric product into a vector, but at the same time prevents circularization of the oligomerized DNA. Four illustrative example of suitable initiator adaptors are shown below:

Example 9

Initiator Adaptor GACA-Bam for BamH I Oligomers

```
5'pGACACACGTGCTAGTCCG         SEQ ID NO: 21
    GTGCACGATCAGGCCTAG-5'     SEQ ID NO: 22
```

Example 10

Initiator Adaptor GACA-Pst for Pst I Oligomers

```
5'pGACACACGTGCTAGTCCCTGCA     SEQ ID NO: 23
    GTGCACGATCAGGG-5'         SEQ ID NO: 24
```

Example 11

Initiator Adaptor CTGA-Bam for BamH I Oligomers

```
5'pCTGACACGTGCTAGTCCG         SEQ ID NO: 25
    GTGCACGATCAGGCCTAG-5'     SEQ ID NO: 26
```

Example 12

Initiator Adaptor CTGA-Pst for Pst I Oligomers

```
5'pCTGACACGTGCTAGTCCCTGCA     SEQ ID NO: 27
    GTGCACGATCAGGG-5'         SEQ ID NO: 28
```

Initiator adaptors are produced from two complementary chemically synthesized oligonucleotides annealed to form the illustrated double strand adaptors. At one terminus, the adaptors have a palindromic cohesive complementary end for ligation to either BamH I or Pst I generated sequence tag monomers and initiate oligo formation. An asymmetric cohesive end (either 5'-GACA-3' or 5'-CTGA-3') is present at the other adaptor terminus for specific ligation into one or the other cloning site on the multiplex sequencing vector, pSLGVT-3. The unique design of pSLGVT-3 and other plasmids of the pSLGVT-series have the capacity to carry two independent DNA inserts.

Complementary cohesive end to the monomer at only one terminus of the initiation adaptor restricts ligation of monomer and the growth of the oligomer in one direction, thereby minimizes the formation of unproductive circular molecules. The lower strand of the initiation adaptors is unphosphorylated to prevent adaptor dimer formation. Oligomer formation is carried out in the presence of excess GVT-pair monomers to initiator adaptor in a ligation reaction that is allowed to go to completion. The principal products produced are a collection of oligomerized monomers "capped" at both ends by initiator adaptor. The ratio of DNA monomer to initiator adaptor dictates the overall size range of the final oligomerized product. A productive ratio is derived by titration using as a starting point, one part initiation adaptor to N parts monomer; where N equals (the average number of monomer desired in the final product plus 2)/2. If necessary, several ligation reactions employing a range of initiator adaptor to monomer ratios can be pooled and desired length product purified by gel electrophoresis. Conditions are chosen to yield oligomerized species from the GAGC- and GTGA-initiator adaptors comprising approximately twenty five to thirty copies (~4.6 to 2 kb in length), which are purified on 1.5% agarose gel and cloned into the two sites of sequencing vector, pSLGVT-3.

8. Cloning Oligomerized GVT-Pair Monomers into Multiplex Sequencing Vector, pSLGVT-3

As used herein, the term multiplex sequencing vector refer to a plasmid vector optimized for high-throughput Sanger dideoxy sequencing that has the capacity to carry an independent insert in each of two DNA cloning cassettes resulting in four sequencing reads from each of four primer binding sites.

pSLGVT-3 (or its low copy number variant, pSLGVT-2) is digested with Eco31 I and Esp3 I to produce to yield two vector segments, which are purified by gel electrophoresis for use. Vector segment 1 comprises the plasmid replicon module and has 5'TCAG-3' and a 5'-TGTC-3' cohesive ends. Vector segment 2 comprises the Kan module and has 5'-TGTC-3' and 5'-TCAG-3' overhangs. Vector segment 1 is ligated with equal molar equivalent of oligomerized GVT-pairs produced by initiator adaptor GACA-. In a separate reaction, vector segment 2 is ligated to equal molar equivalent of oligomerized GVT-pairs produce by initiator adaptor CTGA-. After one-hour incubation the two ligation reactions are combined and reincubated to assemble the desired circular product comprising two independently derived inserts of oligomerized GVT-pairs, ligated between the two vector segments.

A typical sequence read lengths of 600 to 800 bp is sufficient to determine the sequence of at least 10 GVT-pairs. Based on the determination of 10 GVT-pairs per sequencing read and four sequencing reads from a single template, a single plasmid template of the present invention would generate the sequences of more than 40 GVT-pairs. Fosmid paired-end mapping with end-pair spacing of 40 kb requires 75,000 fosmid end-pairs spaced hypothetically end to end to cover the human genome at a cost of 75,000 fosmid template preparations and 150,000 sequencing reads. In comparison, one-fold coverage of the Human Genome at similar 40 kb spacing between GVTs by the use of the present invention would require 75,000 GVT-pairs produced at a cost of only 7,500 sequencing reads, and 1,875 plasmid template preparation. For a similar level of genomic coverage and resolution, the methods of the present invention enjoy a factor of twenty or more reduction in sequencing reads and a factor of forty or more reduction in template preparation when compared to the fosmid paired-end method of Tuzun et al. (*Nat Genet* 37:727 (2005)).

PREFERRED EMBODIMENTS OF INVENTION

Evidence mounts that genetic structural variations comprise millions of base-pairs of heterogeneity in Man and is a major component of our genetic diversity some of which are almost certain to negotiate our interaction with the environment and play a role in disease, disease susceptibility or progression. The present invention relates to systems, methods, compositions, vectors, vector components and kits to create pairs of linked genomic sequence tags for the rapid generation of high-resolution genetic maps to identify such genomics variations.

In a preferred embodiment, the present invention identifies fine-structural-variations within a target genome through the creation of a plurality of GVT-pairs of unique genomic positional identifiers of defined spatial distance and orientations. The GVT-pairs collectively represent the genomic profile of the subject, which when compared with a reference sequence or to similarly produce genomic profiles of other target genomes, denote the presence of fine-structural-differences between nucleic acid populations. Genomic fine-structural-variations detectable by the present invention includes: deletion and insertions, duplication, inversions, translocation and other chromosomal rearrangements. The present invention offers means to identify these genomic features at a user defined resolution level dictated by the experimental design.

Assuming uniform distribution of the four bases, an 18-bp or 27-bp GVT of the present invention should occur by chance on average once every $4^{18}$ and $4^{27}$ base pairs, respectively, and should represent unique sequence identifiers in the human and other complex genomes. Unambiguous assignment of GVT to the genome improves when separation distance between GVTs is considered. For example, a GVT-pair comprising two spatially linked 18-bp GVTs produced from a size-fractionated target DNA population is effectively a 36-bp sequence tag. Similarly, a linked pair of 27-bp GVT is functionally a 54-bp sequence tag. Despite the tag length, it might not be possible to assign a very small set of GVT or GVT-pairs to a unique genomic position, such as those residing completely within repetitive elements. Regions of the genome that are retractile to analysis by the present invention are expected to be small and can be modeled by computational methods known in the art.

The common framework sequence present on each GVT-pair monomer allows unambiguous extraction of GVT-pair sequences from the high-throughput sequence data. Discordance between GVT-pairs to one or more reference sequences is revealed by alignment using MEGABLAST (Zhang et al. *J Comput Biol* 7:203 (2000)) or similar computer programs. Discordance of the GVT-pair separation distance or orientation with the reference over a threshold level signals the presence of a structural difference between target and reference DNA. The threshold level is set by the experimental design, two standard deviations over the mean GVT separation distance being a reasonable default value. Deletions in the target DNA may be defined by two or more GVT-pairs spanning greater than two standard variations from the mean separation distance when compared to the reference sequence. Accordingly, insertions in the target DNA may be defined as sites where two or more GVT-pairs spanning less than two standard variations from the mean separation when compared to the reference sequence. Inversions in target DNA are defined as sites where two or more GVT-pairs having inconsistent orientation of their GVTs. Discordant GVT-pairs are manually curated and assessed before proceeding to validation by PCR, Southern blot hybridization analysis or by insert isolation and sequencing.

Target genomic nucleic acids of the invention can be derived from any source including: genomic DNA of eukaryotic, prokaryotic organisms, microbes, plastids, and viruses. Target genomic nucleic acids of the present invention can also be derived from RNA genome of organisms such as the RNA viruses through a reverse-transcription process to convert RNA to DNA. The choice of target nucleic acids for investigation may be influenced by prior knowledge of association of a particular chromosome or chromosome region with certain disease conditions described in the scientific literature. The present invention can utilize target DNA from isolated chromosomes or chromosome regions. The present invention can be used in broad whole genome-wide scans of patient cohorts at a range of resolutions to suit the study design. Methods for the purification of chromosome, chromosome segments, genomic DNA and RNA are known in the art. Also known in the art are methods to amplify nucleic acids by PCR or by other means to produce target DNA for analysis by the present invention.

Methods to cleave target DNA and to fractionate target the DNA to a desired size for setting the spatial distance between GVTs of a GVT-pair are described in an earlier section of this disclosure. Hydrodynamic shearing or partial enzymatic digestion of DNA with frequent cutting enzymes can be used to produce a population of DNA fragments with a high degree of overlapping fragments for maximal coverage every region of the target DNA. Alternatively, target DNA can be digested to completion with several restriction endonucleases in separate cleavage reactions and then size-fractioned to desired size classes for GVT-pairs production. GVT-pairs produced from size-selected target DNA prepared by completion digestion with a single restriction endonuclease are nonoverlapping and cover only a portion of the target DNA complexity. Size-selected DNA fragments from complete enzymatic digestions with other restriction endonucleases can be used to cover gaps. Cleavage of target DNA randomly or in combination with complete enzymatic digestion to cover a genome of a given complexity can be modeled computationally by workers that are skill in the art to derive a study design to make the optimal use of resources. Enzymes such BamH I, Hind III, Pst I, Spe I and Xba I are insensitive to CpG methylation and would cleave mammalian genomic DNA at every site to produce GVT-pairs that accurately represent pairs of adjacent recognition sites for those enzymes. Other suitable enzymes that are insensitive to the effect of CpG methylation, overlapping CpG methylation or other kinds of DNA modifications that may influence nucleic acid analysis by the present invention have been described in the literature (May et al. *J Bacteriol* 123:768, (1975); Hallman et al. *J Mol Biol* 126:367, (1978); Buryanov et al. *FEBS Letters* 88:251, (1978); Geier et al. *J Biol Chem* 254:1408, (1979); Kan et al. *J Mol Biol* 130:191, (1979); McClelland et al. *Nucleic Acid Res* 22:3640, (1994)) and by major vendors of restriction endonucleases (Fermentas, Hanover, Md.; New England Biolabs, Ispwich, Mass.). In certain embodiments, the use of enzymes whose cleavage of target DNA is sensitive to DNA modifications may be used to demarcate sites of modifications in the target DNA. For example, the present invention can identify sites of DNA methylation, which are known to regulate gene expression. For such an application, target DNA is digested to completion with a methylation sensitive restriction enzyme and GVT-pairs produced from the digested DNA. Sites of methylation are identified by discordance of the resulting GVT-pairs when compared to adjacent restriction sites on the reference sequence.

Discordant GVT-pairs are first manually curated before proceeding to a series of hierarchical filters for validation. In cases where the discordant GVT-pairs are produced from size-selected DNA derived from complete restriction endonuclease digestion, Southern blot analysis of target DNA and reference DNA digested with the same restriction endonuclease could be used to validate differences in marker distance between target and reference DNA. The GVTs are of sufficient length for use as PCR primers to isolate the intervening genomic sequence for shotgun sequencing to determine the precise nature of the structural variation.

It is believed the study of structural variations will shed new light on complex diseases, such as obesity and diabetes, whose development is triggered by the interactions of genes, genetic elements and the environment. The choice of nucleic acids for analysis by the present invention may be influenced by prior knowledge of association of a particular chromosome or chromosome region with certain disease conditions described in the scientific literature. The present invention can target DNA from isolated chromosomes or chromosome regions or tissue samples at high resolution. Alternatively, the present invention can be used in broad whole genome-wide scans of patient cohorts at a range of resolutions to suit the study design. The current technique of fosmid paired-end sequencing requires over a million sequence reads to analyze each individual at a moderate level of resolution and coverage, thereby limiting its use as a platform to scan large populations for association studies to find biomarkers that are diagnostic or prognostic to disease outcome as well as potential drug targets for medical intervention. The present invention offers a solution to these limitations, and as such it has the potential to create new medical diagnostics and to aid drug discovery.

In another preferred embodiment, fine-structural-variations identified by the present invention are used to design oligonucleotide array assays, microarray assays PCR-based assays and other diagnostic assays in the art to detect differences between nucleic acid populations. Present microarrays and oligonucleotide arrays are efficient platforms for detection of nucleic acid copy number alterations and single or small nucleotide polymorphisms but are not suited to detect other genomic changes that may contribute or are causal to disease. The identified products of the present invention enable the design of oligonucleotide and microarray assays and other diagnostic assays in the art to screen translocation, insertion, deletion, and inversion junctions that demarcate fine-structural-variations identified by the present invention. These assays could then be used to screen general population and large patient cohorts to determine the role of fine-structural-variations in complex diseases such as obesity, diabetes and many cancers, whose development is triggered by the interactions of multiple genetic and environmental factors. Other uses for these assays include but are not limited to the diagnosis or the differentiation between closely related species, strains, race or biotypes of microorganism with utilities in the fields of medical diagnostic and industrial microbiology.

In another preferred embodiment, the present invention is used to create high-resolution genomic maps to aid genomic assembly from shotgun DNA sequencing. A comprehensive set of unique genetic markers of defined separation distance or of adjacent restriction endonuclease sites would greatly facilitate whole genome sequencing efforts by providing a scaffold for genome assembly. It is expected that a number of GVT-pairs produced by the present invention that are discordant to the present build of the Human Genome Assembly (build 35, May 2004) may not actually represent fine-structural variation in the target DNA, but rather reflect errors or gaps in the current Human Genome Assembly. Further compound the problem is that the current Genome Assembly is derived from DNA of pooled multiple donors. Reference sequences derived from single individuals that are representative of the range of human diversity are needed to move the genomics field forward. The utility offered by the present invention provides the means to do so.

In another preferred embodiment, the present invention is used to create high-resolution genomic maps to facilitate phylogenetic studies and for determining the genetic and functional relationship between closely related organisms. An aspect of the invention especially suited for this application makes use of GVT-pairs produced from target DNA digested to completion with one or more restriction endonucleases alone or in useful combination for GVT-pair production without a DNA size-fractionation step. Essentially, the so produced GVT-pairs constitute a genomic profile comprising pairs of positional markers that demarcate adjacent restriction endonuclease sites along the length of the target DNA. The identity of the GVT-pairs and their relative abundance can be used to create high-resolution genomic profiles that can be used to identify, differentiate and quantify the genome of origin within a complex medical or environmental DNA isolate. The so produced GVT-pairs also has utility in the area of industrial microbiology for identifying genomic differences causal to desirable traits, such as favorable growth rate and the production of useful secondary metabolites and recombinant proteins in closely related strains, biotypes, or race or genetically modified organisms. As such, the present can be used as a tool to aid strain improvement in the industrial production of microbial derived products. High resolution genomic maps produced by the present invention also offer a low cost and effective means to survey the nucleic acids of closely related pathogens to identify regions of variations to target detailed sequence analysis to identify pathogenic determinants that could be used for diagnosis and as drug targets for medical intervention.

In another preferred embodiment, the present invention can be use for genetic dissection of phenotype diversity in farm animals and agricultural crops to facilitate marker-assisted breeding. Farm animals are of a particular interest for identifying the complex genetic elements that contribute to the control of growth, energy metabolism, development, body composition, reproduction and behavior, as well as other traits sought by classical breeding. For a review see Andersson (*Nat Rev Genet* 2:130 (2001)). Most agriculture traits of interest are multi-factorial and are often controlled by an unknown number of quantitative trait loci (QTL). Microsatellite maps for genomic scans have been developed for the major farm animals. Association studies using these markers and the candidate gene approach are the two major strategies used for the identification of QTLs. The cloning of QTLs is challenging since the relationship between genotype and phenotype is considerable more complex than for the monogenic traits. However, it is possible to determine the QTL indirectly by progeny testing where the segregation of the QTLs is deduced using data from genetic markers and phenotypic variations among the progeny. At present, the molecular basis for most QTLs is as yet unknown. QTL mapping in *Drosophila* suggests that QTLs are often associated with sequence variations in the noncoding regions (MacKay *Nat Rev Genet* 2:11 (2001)). As in Man, it is expected that fine-structural-variations in the genomes of farm animals and crop plants will likely play an important role in phenotypic expression and interaction of the genome with the environment. The present invention provides the means to tabulate the comprehensive range of genomic structural diversity in farm animals and crop plants at low cost. The tabulated information would then enable the creation of oligonucleotide microarrays and other diagnostic platforms for use in association and linkage studies to identify and characterize the actual QTLs leading to marker-assisted breeding.

As the major pollinator, bees play a critical role in agriculture and in many parts of the world. Apiculture is another area that stands to benefit from the present invention. The honeybee is an economically important species suited to use genetic technology in breed development. Bees have a short generation time and produce large number of progeny. Lines are also readily propagated by artificial insemination. Bee strains exhibit broad phenotypic variations in productivity, disease resistance and behavioral traits, many of which are under complex genetically control. Important behavioral traits under genetic control include: aggression as exemplified by many African strains, foraging habits, honey yield and the so termed "hygienic" behavior. The "hygienic" trait is regulated by at least seven as yet undefined genetic loci, which in sum result in the cleaning behavior by the hive members to rid dead or disease broods as a primary defense against funal and mite infestation, two major economic bee pathogens. A primary goal is to develop reliable diagnostic molecular markers that could be used in marker-assisted breeding to identify the desired progeny strains quickly and efficiently without the need for complicated and time consuming breeding experiments and field assays. Genetic maps and a reference sequence of the 200 mega-base size genome of *Apis mellifera* strain DH4 (The Honeybee Genome Sequencing Consortium *Nature* 443:931, (2006)) is available for use by the present invention to provides efficient and low cost methods to survey genomes of multiple bee strains for fine-structural-variations at high resolution to correlate desired phenotype to genotype. The ability to survey multiple strains cost effectively is a key advantage offered by the present invention. For example, five-fold coverage of a 200 mega-base bee genome at a 10 kb resolution window would require only 10,000 sequence runs and 2,500 sequencing template preparations. The cost estimate is based on the sequence determination of 10 oligomerized GVT-pairs per sequencing runs and each vector template supporting four independent sequencing reactions.

In another preferred embodiment, the present invention can be used to identify genetic causes underlying neurological disorders and traits. It is generally believed that at least a component of many neurological disorders such as autism, bipolar disorder and schizophrenia have a complex non-Mendelian genetic component (Holzman and Matthysse *Psycholology Sci* 1:270 (1990); Owen and Craddock *Mol Psychiatry* 1: 21 (1996); Craddock and Jones *Br J Psychiatry* 178:s128 (2001)). Complementing linkage and association studies in current use to identify the genomic components, the present invention provides means to assess the contributory role of genomic fine-structural-variations in neurological disorders and may lead to new methods for diagnosis, prognosis and patient management.

In another preferred embodiment, the present invention can be used to identify genetic causes underlying cancer thereby create means for diagnosis, prognosis, and therapeutic intervention. Virtually all cancers are due to abnormalities in DNA sequence, either inherited or acquired through somatic mutations during life. The prevailing tenet of oncogenesis is that together with environmental factors, accumulating DNA mutation alters gene expression or gene functions pass a critical functional threshold that allows clonal expansion, cellular invasion of surrounding tissues and the initiation of metastasis. One in three people in the Western World will develop cancer and one in five will die, making cancer the most common of the genetic diseases. The field historically began with the identification of potent onco- or tumor suppressor genes where a simple loss or gain of function due to small number of nucleotide changes to a locus was the major contributory factor to cancer. The field has since expanded to gene dosage where duplication or deletion of DNA segments resulting in alternation of gene copy number is the presumed cause of oncogenesis. The use of array CGH has been particularly useful for the detection of alteration in DNA copy number and the loss of heterozygosity in cancer cell lines and primary tumors. A comprehensive review of copy number analysis in cancer and a catalogue of somatic mutation in cancer and references therein can be found in under "The Cancer Genome Project" of the Sanger Institute (www.sanger.ac.uk/genetics/CGP).

Most recently, the important role of genomic fine-structural-variations in oncogenesis is recognized. During the course of oncogenesis, the tumor genome accumulates a large number of rearrangements, including amplifications, deletion, translocations, inversions and the like, many of which contribute directly to tumor progression (Gray and Collins *Carcinogenesis* 21: 443 (2000)). Volik et al. (*Genome Research* 16: 394 (2006)) made use of a functional variation of fosmid paired-end mapping to detect all changes in genomic architecture of a progressing tumor, in particular translocations and inversion events that are not detectable by array CGH. Their approach to dissect the breast cancer genome was most informative but was acknowledged by the investigators to be limited by the expense and resources required to obtain end-terminal sequences of the large number of BAC clones for each sample. The present invention offers low cost, high-resolution methods to overcome these deficiencies and to identify genomic fine-structural-variations not amendable to detection by array CGH. The present invention has sufficient low cost to enable use in broad surveys of cancer patient cohorts and for use to track the accumulation of genomic changes in tumor progression in individual patients. The ability to track genomic changes during tumor progression would have profound predictive value in clinical outcome, providing significant improvements in patient management.

In yet another preferred embodiment, the methods described herein can be used to identify mRNA processing variants. The concept of one gene encoding one protein is being superseded with one gene encoding a plurality of proteins, some of which have distinct functions that are medically relevant. The process appears highly regulated and is mediated in part through alternative processing of mRNA as well as by the differential usage of promoters, transcription terminators and post-translational processing. The process of trans-splicing, where two distinct mRNA transcripts recombine, further adds to the transcriptome complexity. The choice of target mRNA for use may be influenced by prior knowledge of certain disease condition, cell types, organ or developmental stage where certain mRNA variants may be of importance.

Those that are skilled in the art are familiar with method for mRNA isolation and the conversion of mRNA to cDNA. Within one aspect of the present invention, isolated RNA is converted to cDNA by reverse-transcription or reverse-transcription coupled with PCR by methods including the use of a random primer containing a restriction endonuclease such Mme I, CstM I, NmeA III or EcoP15 I. The restriction site is situated on the primer such that digestion of the resulting double stand cDNA with the said endonuclease removes the primer sequence from the cDNA. Primer concentration is adjusted to yield average size products of 300 to 500 bp or in accordance to the experimental design. Following repair of the cDNA ends using T$_4$ DNA polymerase, the cDNA is dephosphorylated and ligated to a suitable GVT-adaptor and size-selected on a 5% acrylamide gels for the production of GVT-pairs. mRNA processing variants are identified discordance of the GVT-pair with the NCBI Reference Sequence (RefSeq) or other databases. Processing variants are validated by PCR using primers derived from the discordant GVT-pairs.

I claim:

1. A method for producing juxtaposed genomic variation tags (GVTs) for determining fine-structural-variations, wherein the juxtaposed GVTs comprise two constituent members of a tag pair (GVT-pair) of a target nucleic acid molecule, the method comprising:
   a) providing a target nucleic acid molecule;
   b) fragmenting the target nucleic acid molecule to form one or more fragmented target DNA inserts;
   c) providing a DNA adaptor, comprising at least one restriction endonuclease recognition sequence, wherein the restriction endonuclease recognition sequence is located at a predetermined sequence position on the DNA adaptor;
   d) ligating a DNA adaptor to each end of the fragmented target DNA insert, thereby forming an adaptor-ligated DNA insert, wherein the location of the restriction endonuclease recognition sequence on each DNA adaptor directs cleavage of the fragmented target DNA insert at a predetermined distance from each end of the fragmented target insert;
   e) providing a plasmid vector;
   f) ligating each end of the adaptor-ligated DNA insert to one end of the plasmid vector, thereby forming a circular plasmid that carries the adaptor-ligated DNA insert;
   g) digesting the circular plasmid that carries the adaptor-ligated DNA insert using restriction endonuclease molecules that recognize the restriction endonuclease recognition sequences on the DNA adaptors, thereby generating a linear molecule comprising two genomic variation tags (GVTs), wherein each GVT comprises a terminal sequence of the fragmented target DNA insert, and each GVT is attached to one end of the plasmid vector via a DNA adaptor;
   h) recovering said linear molecule comprising two GVTs;
   i) recircularizing said linear molecule by intra-molecular ligation, thereby creating a GVT pair comprising two juxtaposed GVTs;
   j) corresponding the GVT pair to a reference nucleic acid molecule, wherein each GVT corresponds to a segment of the reference nucleic acid molecule;
   k) determining separation distance and orientation between the GVT pair on the target nucleic acid molecule;
   l) determining separation distance and orientation between the segments on the reference nucleic acid molecule; and
   m) determining whether the target nucleic acid molecule has a fine-structural-variation as compared to the reference nucleic acid molecule by comparing the separation distance and orientation between the GVT pair with the separation distance between the segments on the reference nucleic acid molecule.

39

2. A method for producing juxtaposed genomic variation tags (GVTs) for determining fine-structural-variations wherein the juxtaposed GVTs comprise two constituent members of a tag pair (GVT-pair) of a target nucleic acid molecule, the method comprising:
   a) providing a target nucleic acid molecule;
   b) fragmenting the target nucleic acid molecule to form one or more fragmented target DNA inserts;
   c) providing a linear plasmid vector, comprising at least a pair of restriction endonuclease recognition sequences, wherein each restriction endonuclease recognition sequence is located at a predetermined sequence position on each end of the plasmid vector;
   d) ligating each end of the fragmented target DNA insert to each end of the plasmid vector, thereby forming a circular plasmid that carries the fragmented DNA insert, wherein the fragmented target DNA insert is flanked by the pair of restriction endonuclease recognition sequences, and each endonuclease recognition sequence directs cleavage of the fragmented target DNA insert at a distance from each end of the fragmented target insert;
   e) digesting the circular plasmid that carries the fragmented DNA insert using restriction endonuclease molecules that recognize the restriction endonuclease recognition sequences on the plasmid vector, thereby cleaving the target DNA insert and creating a linear molecule comprising two sequence tags (GVTs), wherein each GVT comprises a terminal sequence of the target DNA insert, and each GVT is attached to one end of the plasmid vector;
   f) recovering said linear molecule comprising two GVTs;
   g) recircularizing said linear molecule by intra-molecular ligation, thereby creating a GVT-pair comprising two juxtaposed GVTs
   h) corresponding the GVT pair to a reference nucleic acid molecule, wherein each GVT corresponds to a segment of the reference nucleic acid molecule;
   i) determining separation distance and orientation between the GVT pair on the target nucleic acid molecule;
   j) determining separation distance and orientation between the segments on the reference nucleic acid molecule; and
   k) determining whether the target nucleic acid molecule has a fine-structural-variation as compared to the reference nucleic acid molecule by comparing the separation distance and orientation between the GVT pair with the separation distance between the segments on the reference nucleic acid molecule.

3. A method to create a DNA oligomer through controlled and ordered ligation of short DNA monomers possessing palindromic, rotationally equivalent cohesive ends to yield an oligomeric product bound at both ends by an initiation adaptor, comprising the steps of:
   forming an oligomer of DNA monomers initiated from an initiation adaptor wherein one adaptor terminus has a nonpalindromic cohesive end that cannot self-ligate, but can adhere to a vector, while the other adaptor terminus has a cohesive unphosphorylated end to prevent adaptor dimer formation and is complementary to the cohesive ends of the DNA monomer for ligation to monomer to initiate oligomer formation; and
   terminating oligomer growth upon ligation of either a free initiation adaptor to the oligomer formed by adding the DNA monomers or by ligation of another oligomer initiated by the initiation adaptor;
   wherein the oligomer so formed has an average length regulated by a molar ratio of DNA monomer to initiation adaptor measured when commencing formation of the oligomer.

4. The method according to claim 1, wherein the two constituent members of the tag pair flank two adjacent and cleavable restriction endonuclease sites for one or more restriction endonucleases in the target nucleic acid molecule.

5. The method of claim 1, wherein the target DNA insert is genomic DNA, cDNA, viral DNA, microbial DNA, plastid DNA, chemically synthesized DNA, a DNA product of nucleic acid amplification, or DNA transcribed from RNA.

6. The method of claim 1, wherein the target nucleic acid molecule is fragmented, either randomly by the application of mechanical force or by partial digestion with one or more enzymes, to form one or more fragmented target DNA inserts.

7. The method of claim 1 or 2, wherein the target nucleic acid molecule is fragmented by complete digestion using one or more restriction endonucleases alone or in combination to form one or more fragmented target DNA inserts.

8. The method of claim 1 or 2, wherein the fragmented target DNA insert is size fractionated.

9. The method of claim 1 or 2, wherein the fragmented target DNA insert is not size fractionated.

10. The method of claim 1 or 2, wherein a restriction endonuclease used to create the GVT pair is Mme I, NmeA III, CstM I, BceA I, Bpm I, BpuE I, Bsg I, BsmF I, BstV1 I, Eco57 I, Eco57M I, or Gsu I.

11. The method of claim 10, wherein the restriction endonuclease is Mme I.

12. The method of claim 10, wherein the restriction endonuclease is CstM I.

13. The method of claim 10, wherein the restriction endonuclease is NmeA III.

14. The method of claim 1 or 2, wherein a restriction endonuclease used to create the GVT pair is EcoP 15 I, EcoP 1 I, Pst II, HinFIII, StyLT I, L1aF I, BceS I, Hine I, PhaB I, Hpy790545P, Hpy790639 I, or HpyAXIP.

15. The method of claim 14, wherein the restriction endonuclease is EcoP15 I.

16. The method of claim 14, wherein the restriction endonuclease is Pst II.

17. The method of claim 1 or 2, wherein a type IIS or type IIG restriction endonuclease is used to create the GVT pair and recognizes a six or more base pair uninterrupted recognition sequence.

18. The method of claim 1 or 2, wherein a type III restriction endonuclease is used to create the GVT pair and recognizes a six or more base pair uninterrupted recognition sequence.

19. The method of claim 2, wherein the target DNA insert is genomic DNA, cDNA, viral DNA, microbial DNA, plastid DNA, chemically synthesized DNA, DNA product of nucleic acid amplification, or DNA transcribed from RNA.

20. A method for creating DNA sequence tag oligomers, comprising:
   a) providing an amount of DNA sequence tag monomers, wherein each DNA sequence tag monomer comprises two cohesive ends, each cohesive end being complementary to a cohesive end of another DNA sequence tag monomer;
   b) providing an amount of DNA initiation adaptors, each comprising a nonpalindromic cohesive end that cannot self-ligate and an unphosphorylated palindromic cohesive end that is complementary to a cohesive end of the DNA sequence tag monomers, wherein the DNA sequence tag monomers are provided in an excess molar amount as compared to the DNA initiation adaptors; and c) contacting the excess molar amount of the DNA sequence tag monomers with the DNA initiation adaptors, thereby forming an initiation adaptor-ligated DNA sequence tag oligomer comprising a series of DNA sequence tag monomers ligated one to another, and wherein each end of the series of ligated DNA sequence tag monomers is attached to the nonpalindromic cohesive end of a DNA initiation adaptor.

21. The method according to claim 20, wherein each DNA sequence tag monomer comprises a GVT-pair.

22. The method according to claim 20, wherein a predetermined excess molar amount of the DNA sequence tag monomers are contacted with a predetermined molar amount of DNA initiation adaptors, thereby forming initiation adaptor-ligated DNA sequence tag oligomers that comprise, on average, a desired number of DNA sequence tag monomers, the desired number being related to the molar ratio of DNA initiation adaptors to DNA sequence tag monomers, wherein the molar ratio can be calculated as one part initiation adaptor to N parts monomer, where N equals (the desired number plus 2) divided by 2.

23. The method according to claim 21, further comprising:
d) providing a plasmid vector comprising a cohesive end that is complementary to the nonpalindromic cohesive end of the DNA initiation adaptors; and
e) ligating the plasmid vector to said oligomer, thereby forming a plasmid vector that carries the initiation adaptor-ligated DNA sequence tag oligomer.

24. A method for producing a multiplex sequencing vector that carries DNA sequence tags of interest, comprising:
a) providing a plurality of DNA sequence tags of interest,
b) providing a circular plasmid vector comprising a plurality of vector modules, wherein more than one of said vector modules comprise a type IIS endonuclease recognition sequence and a pair of DNA sequencing primer binding sites for priming Sanger dideoxy sequencing reactions, wherein the endonuclease recognition sequence directs cleavage of those more than one vector modules at a predetermined cleavage site on each module, and each side of said cleavage site is flanked by a DNA sequencing primer binding site;
c) digesting the circular plasmid vector using restriction endonuclease molecules that recognize the endonuclease recognition sequence on said more than one vector modules, thereby forming linear plasmid vectors;
d) ligating an end of a DNA sequence tag of interest to an end of each linear plasmid vector; and
e) reforming a circular plasmid vector from said linear plasmid vectors, thereby generating a circular multiplex sequencing vector that carries a plurality of the DNA sequence tags of interest.

25. The method according to claim 24, wherein each DNA sequence tag comprises a GVT-pair or a GVT-pair-oligomer.

26. The method according to claim 24, wherein the circular plasmid vector comprises a vector module comprising a drug selectable marker.

27. The method according to claim 24, wherein the circular plasmid vector comprises a vector module comprising a plasmid replicon for plasmid replication.

28. The method according to claim 24, wherein digestion of a vector module using restriction endonuclease molecules that recognize an endonuclease recognition sequence creates a nonpalindromic cohesive end.

29. The method according to claim 24, wherein the circular plasmid vector comprises a vector module that is free of recognition sites for Mme I, CstM I, NmeA III, EcoP15 I, Pst II, BamH I, Pst I, BspT I, or Kas I, and said vector module comprises Eco31 I and Esp3 I recognition sites.

30. The method of claim 1, further comprising isolating the created GVT-pair by restriction endonuclease digestion at sites that are on each DNA adaptor and are flanking the created GVT-pair.

31. The method of claim 2, further comprising isolating the created GVT-pair by restriction endonuclease digestion at sites that are on the plasmid vector and are flanking the created GVT-pair.

32. The method according to claim 1, further comprising determining whether the target nucleic acid molecule has inversion by
generating at least two GVT-pairs of the target nucleic acid molecule;
determining orientation of each GVT pair; and
comparing the orientation of each GVT-pair;
wherein inconsistent orientation between the GVT-pairs indicates that the target nucleic acid molecule has inversion.

33. The method according to claim 2, further comprising determining whether the target nucleic acid molecule has inversion by
generating at least two GVT-pairs of the target nucleic acid molecule;
determining orientation of each GVT pair; and
comparing the orientation of each GVT-pair;
wherein inconsistent orientation between the GVT-pairs indicates that the target nucleic acid molecule has inversion.

34. The method of claim 26, wherein the drug selectable marker is free of Mme I, CstM I, NmeA III, EcoP15 I, Pst II, BamH I, Pst I, BspT I, or Kas I restriction endonuclease sites.

35. The method of claim 26, wherein the drug selectable marker codes for kanamycin resistance.

36. The method of claim 26, wherein the drug selectable marker codes for ampicillin resistance.

37. The method of claim 27, wherein the plasmid replicon is free of Mme I, CstM I, NmeA III, EcoP15 I, Pst II, BamH I, Pst I, BspT I, or Kas I restriction endonuclease sites.

38. The method of claim 27, wherein the plasmid replicon is P15A.

39. The method of claim 27, wherein the plasmid replicon is ColE1.

40. The method of claim 27, wherein the plasmid replicon is a ColE1 derivative of pUC.

41. The method of claim 24, wherein the circular plasmid vector comprises a vector module comprising a cloning site that is created by digestion of the vector module with a type II, type IIS, or a type IIG restriction endonuclease that recognizes a six or more base pair uninterrupted sequence.

* * * * *

UNITED STATES PATENT AND TRADEMARK OFFICE
CERTIFICATE OF CORRECTION

| | | |
|---|---|---|
| PATENT NO. | : 7,932,029 B1 | Page 1 of 2 |
| APPLICATION NO. | : 11/649587 | |
| DATED | : April 26, 2011 | |
| INVENTOR(S) | : Lok | |

It is certified that error appears in the above-identified patent and that said Letters Patent is hereby corrected as shown below:

Column 4,
Line 53, "the actually fragments" should read --the actual fragments--.
Line 63, "endonculease" should read --endonuclease--.

Column 6,
Line 25, "type JIG or" should read --type IIG or--.

Column 11,
Line 31, "(Mme O-adaptor" should read --(Mme I)-adaptor--.

Column 12,
Line 42, "JIG restriction" should read --IIG restriction--.

Column 14,
Line 12, "type HS" should read --type IIS--.

Column 17,
Line 19, "5"-GAGA-3'" should read --5'-GAGA-3'--.

Column 18,
Line 54, "is based the" should read --is based on the--.

Column 22,
Line 23, "(~4.6 to 2 kb" should read --(~1.6 to 2 kb--.

Column 24,
Line 39, "that are skill in" should read --that are skilled in--.
Line 49, "Hallman" should read --Hattman--.

Signed and Sealed this
Sixteenth Day of August, 2011

David J. Kappos
*Director of the United States Patent and Trademark Office*

CERTIFICATE OF CORRECTION (continued)
U.S. Pat. No. 7,932,029 B1

<u>Columns 25-26,</u>
Lines 67-1, "Further compound" should read --Further compounding--.

<u>Column 26,</u>
Line 53, "considerable more" should read --considerably more--.

<u>Column 28,</u>
Line 12, "can be found in under" should read --can be found in--.